United States Patent
Mallet et al.

(10) Patent No.: US 11,114,668 B2
(45) Date of Patent: Sep. 7, 2021

(54) ELECTRODE MATERIALS AND PROCESSES FOR THEIR PREPARATION

(71) Applicants: HYDRO-QUÉBEC, Montréal (CA); MURATA MANUFACTURING CO., LTD., Nagaokakyo (JP)

(72) Inventors: Charlotte Mallet, Montreal (CA); Sylviane Rochon, Saint-Adelphe (CA); Jean-Christophe Daigle, St-Bruno-de-Montarville (CA); Narumi Arai, Nagaokakyo (JP); Shinichi Uesaka, Nagaokakyo (JP); Karim Zaghib, Longueuil (CA)

(73) Assignees: HYDRO-QUÉBEC, Québec (CA); MURATA MANUFACTURING CO., LTD., Nagaokakyo (JP)

( * ) Notice: Subject to any disclaimer, the term of this patent is extended or adjusted under 35 U.S.C. 154(b) by 0 days.

(21) Appl. No.: 16/485,490

(22) PCT Filed: Feb. 15, 2018

(86) PCT No.: PCT/CA2018/050172
§ 371 (c)(1),
(2) Date: Aug. 13, 2019

(87) PCT Pub. No.: WO2018/148833
PCT Pub. Date: Aug. 23, 2018

(65) Prior Publication Data
US 2020/0052302 A1    Feb. 13, 2020

Related U.S. Application Data

(60) Provisional application No. 62/459,309, filed on Feb. 15, 2017.

(51) Int. Cl.
*H01M 4/02* (2006.01)
*H01M 4/62* (2006.01)
(Continued)

(52) U.S. Cl.
CPC .......... *H01M 4/624* (2013.01); *C07D 403/04* (2013.01); *H01G 11/28* (2013.01); *H01G 11/46* (2013.01);
(Continued)

(58) Field of Classification Search
CPC ....................................................... H01M 4/02
See application file for complete search history.

(56) References Cited

U.S. PATENT DOCUMENTS 2,665,323 A    1/1954  Mcfarlane et al.
10,586,986 B2  3/2020  Lecuyer et al.
(Continued)

FOREIGN PATENT DOCUMENTS

CN    105206838 A    12/2015
EP    2876709 A1      5/2015
(Continued)

OTHER PUBLICATIONS

Yao et al. ("Indigo Dye as a Positive-electrode Material for Rechargeable Lithium Batteries" Research Institute for Ubiquitous Energy Devices, National Institute of Advanced Industrial Science and Technology (2010)).*

(Continued)

*Primary Examiner* — Jacob B Marks
(74) *Attorney, Agent, or Firm* — Buchanan Ingersoll & Rooney P.C.

(57) ABSTRACT

This application describes an electrode material comprising an indigoid compound, i.e. indigo blue or a derivative thereof, for instance, together with particles of an electrochemically active material dispersed in a binder. Processes for the preparation of the electrode material and electrodes containing the material, as well as to the electrochemical cells and their use are also contemplated.

25 Claims, 26 Drawing Sheets

(51) Int. Cl.
*C07D 403/04* (2006.01)
*H01G 11/28* (2013.01)
*H01G 11/46* (2013.01)
*H01G 11/48* (2013.01)
*H01G 11/50* (2013.01)
*H01G 11/68* (2013.01)
*H01G 11/86* (2013.01)
*H01M 10/0525* (2010.01)

(52) U.S. Cl.
CPC ............ *H01G 11/48* (2013.01); *H01G 11/50* (2013.01); *H01G 11/68* (2013.01); *H01G 11/86* (2013.01); *H01M 10/0525* (2013.01)

(56) References Cited

U.S. PATENT DOCUMENTS

| | | |
|---|---|---|
| 2011/0159360 A1 | 6/2011 | Hirota et al. |
| 2015/0118559 A1 | 4/2015 | Ito et al. |
| 2015/0146346 A1 | 5/2015 | Shimomura et al. |

FOREIGN PATENT DOCUMENTS

| | | | |
|---|---|---|---|
| JP | 2008084786 A | | 4/2008 |
| JP | 2013025949 A | | 2/2013 |
| JP | 2013-080639 | * | 5/2013 |
| JP | 2013149416 A | | 8/2013 |
| JP | 2016081704 A | | 5/2016 |
| WO | 2016/087759 A1 | | 6/2016 |

OTHER PUBLICATIONS

Andrea Paolella et al., "Light-assisted delithiation of lithium iron phosphate nanocrystals towards photo-rechargeable lithium ion batteries", Nature Communications, 2017, vol. 8, pp. 1-10.
Bernhard Häupler et al., "Carbonyls: Powerful Organic Materials for Secondary Batteries", Advanced Energy Materials, 2015, pp. 1-34.
International Search Report (PCT/ISA/210) dated May 3, 2018, by the Canadian Patent Office as the International Searching Authority for International Application No. PCT/CA2018/050172.
Lan-Hua Yi et al., "Cathodic adsorption voltammetric determination of indirubin at carbon paste electrode", Fenxi Shiyanshi, 2008, 2 pages.
Masaru Yao et al., "Indigo Dye as a Positive-electrode Material for Rechargeable Lithium Batteries", Chem. Lett., 2010, pp. 950-952.
Written Opinion (PCT/ISA/237) dated May 3, 2018, by the Canadian Patent Office as the International Searching Authority for International Application No. PCT/CA2018/050172.
Yanliang Liang, et al., "Organic Electrode Materials for Rechargeable Lithium Batteries", Advanced Energy Materials, 2012, pp. 742-769.
Yuchi Tsao et al., "Enhanced Cycling Stability of Sulfur Electrodes through Effective Binding of Pyridine-Functionalized Polymer", ACS Energy Letters, 2017, pp. 2454-2462.
Yao M. et al.,"Indigo carmine: An organic crystal as a positive-electrode material for rechargeable sodium batteries" Scientific Reports, 2014, vol. 4, No. 3650, pp. 1-6.
Tanoue et al.,"A facile synthesis of 6,60- and 5,50-dihalogenoindigos" Elsevier, Dyes and Pigments, vol. 62, 2004, pp. 101-105.
Klimovich I.V., J.,"Design of indigo derivatives as environment-friendly organic semiconductors for sustainable organic electronics" Journal of Materials Chemistry C, Mat. Chem., 2014, vol. 2, pp. 7621-7631.
Horn, R.H., et al., Notes. The Preflaration of Some 1-Chloroalkane-I-carboxylic Acids, Journal of the Chemical Society (Resumed), 1950, pp. 2900-2908.
Voß, G., et al."Regioselektiver BromlLithium-Austausch bei 2,5-Dibrom-I-nitrobenzol.—Eine einfache Synthese von 4-Brom-2-nitrobenzaldehyd und 6,6'-Dibromindigo" Chemische Berichte, 1989, vol. 122, No. 6, pp. 1199-1201.
Baltac, T., et al., "The Synthesis of Some Food Dyes for Natural and Synthetic Fibres" Revista de Chimie, 2012, vol. 63, No. 6, pp. 618-620.
Bailey, J.E., et al."Synthesis and Purification of Trisulphoindigo and Reversed-Phase High Performance Liquid Chromatographic Determination of Trisulphoindigo in FD & C Blue No. 2" Dyes and Pigments, 1985, vol. 6, No. 2, pp. 135-154.
Leclerc, S., et al.,"Indirubins Inhibit Glycogen Synthase Kinase-3b and CDK5/P25, Two Protein Kinases Involved in Abnormal Tau Phosphorylation in Alzheimer's Disease" J. Biol. Chem., 2001, vol. 276, No. 1, pp. 251-260.
Karapetyan G. et al."Synthesis and Bioactivity of Carbohydrate Derivatives of Indigo, Its Isomers and Heteroanalogues" Chem, Med. Chem., 2011, vol. 6, pp. 25-37.
Extended European Search Report dated Oct. 14, 2020, issued by the European Patent Office in corresponding European Application No. 18753560.4-1108, (6 pages).

* cited by examiner (a)

(b)

(a)

(b)

ELECTRODE MATERIALS AND PROCESSES FOR THEIR PREPARATION

RELATED APPLICATION

This application claims priority to U.S. provisional application No. 62/459,309 filed on Feb. 15, 2017, the content of which is incorporated herein by reference in its entirety for all purposes.

TECHNICAL FIELD

The technical field generally relates to electrode materials and processes for their preparation, for instance, electrode materials comprising an electrochemically active material and an organic additive. The present application also relates to the use of the electrode materials for the preparation of electrodes and their use in electrochemical cells.

BACKGROUND

Indigo blue is a pigment originally extracted from plants which has been used as a dye for centuries. The molecule itself has been studied for various aspects, including its ambipolar organic semiconductor properties.

The indigo blue dye, which is basically insoluble in water, has also been reduced to its colorless and soluble leuco-indigo form (indigo white). This redox property has been more recently studied in electrochemistry. For instance, indigo carmine, an analog of indigo blue, was tested as a purely organic cathode active material in rechargeable batteries (Yao M. et al., Scientific Reports, 4, 3650, pages 1-6).

SUMMARY

In one aspect, the present application relates to an electrode material comprising particles of an electrochemically active material and an indigoid compound, for instance, a compound of any one of Formulae I to IV:

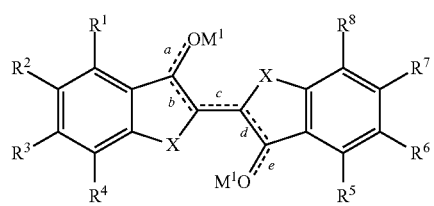

Formula I

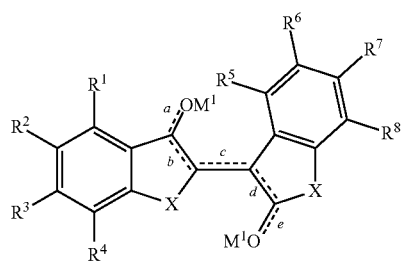

Formula II

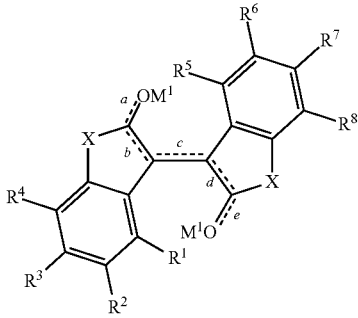

Formula III

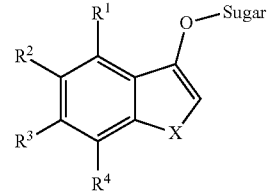

Formula IV wherein,
$R^1$, $R^2$, $R^3$, $R^4$, $R^5$, $R^6$, $R^7$, and $R^8$ are each independently selected from a hydrogen atom, a group selected from halogen (e.g. F), optionally halogenated alkyl, cycloalkyl, or aryl, —CN, —$NO_2$, —$SO_2OM^2$, —OP(O)($OM^2)_2$, —P(O)($OM^2)_2$, or —C(O)$OM^2$, wherein $M^2$ is a cation of an alkali or alkaline earth metal, or a —OC(O)alkyl, —$SO_2NH_2$, —$SO_2$NHalkyl, or —$SO_2$N(alkyl$)_2$, group; and X is, independently in each occurrence, selected from O, S, NH, $NR^9$, and PH (e.g. X is O, S or NH, or X is NH), wherein $R^9$ is selected from natural or synthetic carbohydrate and protective groups, for instance an amine protective group such as trifluoroacetamide, t-butyloxycarbonyl (Boc), benzyloxycarbonyl (Cbz), 9-fluorenylmethyloxycarbonyl (Fmoc), benzyl (Bn), and the like;

Sugar is a natural or synthetic carbohydrate (e.g. mono or disaccharide, oligo and polysaccharides, e,g, β-D-glucose or cellulose); and
wherein:
i. a, c and e are single bonds, b and d are double bonds, and $M^1$ is H or a cation of an alkali or alkaline earth metal thereby forming a salt with the oxygen atom it is linked to negatively charged (e.g. $M^1$ is $Li^+$, $Na^+$, $K^+$, $Ca^{2+}$, or $Mg^{2+}$) wherein the ratio of cation to the rest of the compound of Formula I provides electroneutrality (e.g. $M^1$ may be $Li^+$ or ($Mg^{2+})_{1/2}$); or
ii. a, c and e are double bonds, b and d are single bonds, and $M^1$ is absent;

or an oxime thereof (i.e. where =$OM^1$ is replaced with =NOH in Formulae I, II or III), a compound of Formula IV where the Sugar is replaced by a hydrogen atom, a geometric isomer (e.g. cis or trans) thereof, or a carbohydrate (mono or disaccharide, oligo and polysaccharides, e,g, β-D-glucose or cellulose) complex or conjugate thereof.

In one embodiment, the compound is of Formula I. In another embodiment, the compound is of Formula II. In a further embodiment, the compound is of Formula III. For instance, $R^2$ and $R^6$ are the same and selected from halogen (e.g. F), optionally halogenated alkyl, —CN, and —$SO_2OM^2$, e.g. —CN. In another example, $R^3$ and $R^7$ are the same and selected from halogen (e.g. F), optionally halogenated alkyl, —CN, and —SO$_2$OM$^2$, e.g. —CN. In one embodiment, each of R$^1$ to R$^8$ are hydrogen atoms.

In another embodiment, the compound is of Formula IV, for instance, wherein R$^2$ is selected from halogen (e.g. F), optionally halogenated alkyl, —CN, and —SO$_2$OM$^2$, e.g. R$^2$ is —CN. In another example, each of R$^1$ to R$^4$ are hydrogen atoms.

In one embodiment, the compound is selected from:

Compound 1

Compound 2

Compound 3

Compound 4

Compound 5

Compound 6

Compound 7

Compound 8

Compound 9

Compound 10

Compound 11

Compound 12

Compound 13

Compound 14

In one embodiment, the compound is indigo blue. In another embodiment, the compound of Formula I is leuco-indigo or a salt thereof. In another embodiment, the compound is selected from indigo, indigo carmine, isoindigo, indigopurpurin and indolinedione. In yet another embodiment, the compound is Compound 6. In a further embodiment, the compound is Compound 7. In another embodiment, the compound is selected from compounds 8 to 10. In a further embodiment, the compound is selected from compounds 1, 8, 11, 12, and 14.

In one embodiment, the electrode material further comprises particles of an anode electrochemically active material. In a different embodiment, the electrode material further comprises particles of a cathode electrochemically active material.

In one embodiment, the electrochemically active material comprises a material selected from the group consisting of titanates, lithium titanates, lithium metal phosphates, vanadium oxides, or lithium metal oxides. For instance, the electrochemically active material is selected from $TiO_2$, $Li_2TiO_3$, $Li_4Ti_5O_{12}$, $H_2Ti_5O_{11}$ and $H_2Ti_4O_9$, or a combination thereof, $LiM'PO_4$ wherein M' is Fe, Ni, Mn, Co, or a combination thereof, $LiV_3O_8$, $V_2O_5$, $LiMn_2O_4$, $LiM''O_2$, wherein M'' is Mn, Co, Ni, or a combination thereof, $Li(NiM''')O_2$, wherein M''' is Mn, Co, Al, Fe, Cr, Ti, or Zr, and combinations thereof. Each of the above active materials may be optionally doped with a compatible element.

For instance, the electrochemically active material is selected from titanates and lithium titanates. According to another example, the electrochemically active material is of the formula $LiM'PO_4$ wherein M' is Fe, Ni, Mn, Co, optionally doped with optionally doped with a compatible element, for instance an element selected from Mg, Al, B, Ti, V, Cr, Cu, Zn, Mo, Sn, Ca, Sr and W, or a combination thereof, for instance, the element is Mg. For instance, the electrochemically active material is $LiFePO_4$ or $LiMn_xFe_{1-x}PO_4$, where $0<x<1$, optionally doped with a compatible element, for instance optionally doped with an element selected from Co, Ni, Mg, Al, B, Ti, V, Cr, Cu, Zn, Mo, Sn, Ca, Sr and W, or a combination thereof, for instance optionally doped with magnesium.

In a further embodiment, the electrochemically active material is $LiM''O_2$, wherein M'' is Mn, Co, Ni, or a combination thereof. For instance, the electrochemically active material is $LiNi_wMn_yCo_zO_2$, where $w+y+z=1$.

According to a further embodiment, the particles are further coated with a conductive agent. In a further embodiment, the electrode material further comprising a conductive agent. In yet another embodiment, the electrode material further comprising a binder, e.g. a water-soluble binder or a non-aqueous polymer binder (e.g. a fluorinated polymer binder such as PVdF or PTFE). For instance, the binder comprises a cellulose-derived binder, and/or a water-soluble binder. In a further embodiment, the compound is in a concentration from 0.1 wt % to 5 wt %, or in a concentration from 0.1 wt % to 2 wt %, in the electrode material.

According to another aspect, the application relates to a process for producing an electrode comprising an electrode material as herein defined, comprising the steps of:
a) mixing, in any order, the compound, the particles of electrochemically active material, and a binder in a solvent (e.g. aqueous or non-aqueous solvent) to obtain a slurry;
b) casting the slurry obtained in step (a) on a substrate (e.g. current collector or separator); and
c) drying the casted slurry.

In one embodiment, the substrate is a current collector consisting of aluminum or an alloy having aluminum as the main component. In another embodiment, the substrate is a conductive polymer.

According to a further aspect, the application relates to an electrode comprising the electrode material as herein defined, on a current collector, or an electrode produced by a process as herein defined. For instance, the current collector is aluminum or an alloy having aluminum as the main component, or the current collector is a conductive polymer.

According to yet a further aspect, the present application relates to an electrochemical cell comprising an electrode as herein defined, an electrolyte and a counter-electrode (an electrode of opposing electrochemical activity). For instance, the electrode is a positive electrode, and the negative electrode comprises an electrochemically active material selected from metallic lithium, lithium alloys (e.g. Li—Na, Li—Mg, Li—Zn, and the like), Si, $SiO_x$, graphite, and a carbon mixture (graphite-$SiO_x$, graphite-Si, carbon-Si, carbon-$SiO_x$). In another example, the negative electrode comprises a lithium titanate as electrochemically active material (e.g. $Li_4Ti_5O_{12}$).

In a further aspect, electrochemical generators and accumulators comprising an electrochemical cell or electrode material as herein defined.

According to a further aspect, the present application also further relates the use of the present electrochemical cells and electrodes, for example, in electrical or hybrid vehicles, or in ubiquitous IT devices, and as supercapacitors, for instance, mobile devices, such as mobile phones, cameras, tablets or laptops, in electric or hybrid vehicles, or in renewable energy storage.

Other features and advantages of the present technology will be better understood upon reading of the description herein below with reference to the appended drawings.

DETAILED DESCRIPTION

Figure 1:
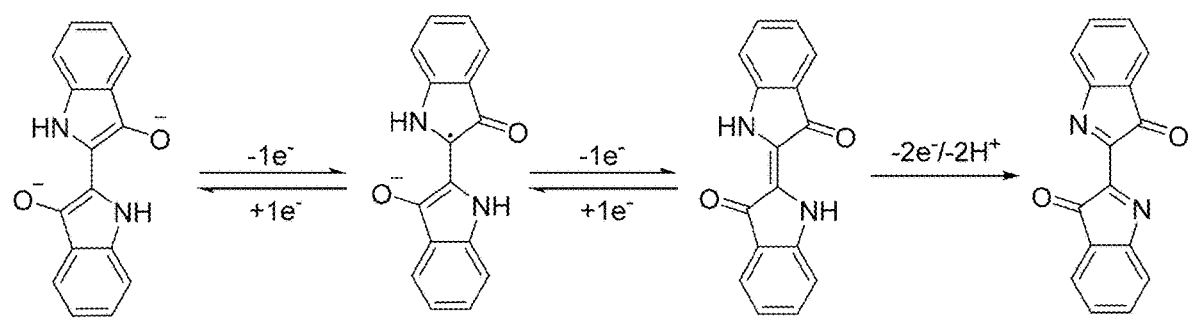
FIG. 1 shows the redox forms of indigo.

This application relates to a process for the preparation of an electrode material containing indigo blue or a derivative thereof, or a reduced form of said indigo blue or derivative, or a salt thereof, and to electrodes produced by such a process.

For instance, the organic additive of the present application may work with Li$^+$, Na$^+$, K$^+$ containing electrolytes. Indigo derivatives such as those used herein may store and release sodium and lithium ions during redox reactions. Organic molecules generally have weak Van der Waals type or π-π type interactions while inorganic molecules possess strong interactions like 3D electrostatic interactions. The property difference results in the organic molecules being more flexible than inorganic molecules, thereby favoring electrochemical storing of larger charge carriers like Na$^+$ ions. Furthermore, physicochemical properties of organic molecules are more easily adjustable.

For example, the present description relates to the use of organic molecules as additives in electrode materials. For instance, the organic molecules are indigoid compounds, i.e. indigo blue or a derivative, leuco-indigo form or salt thereof, i.e. a compound of Formula I, II or III:

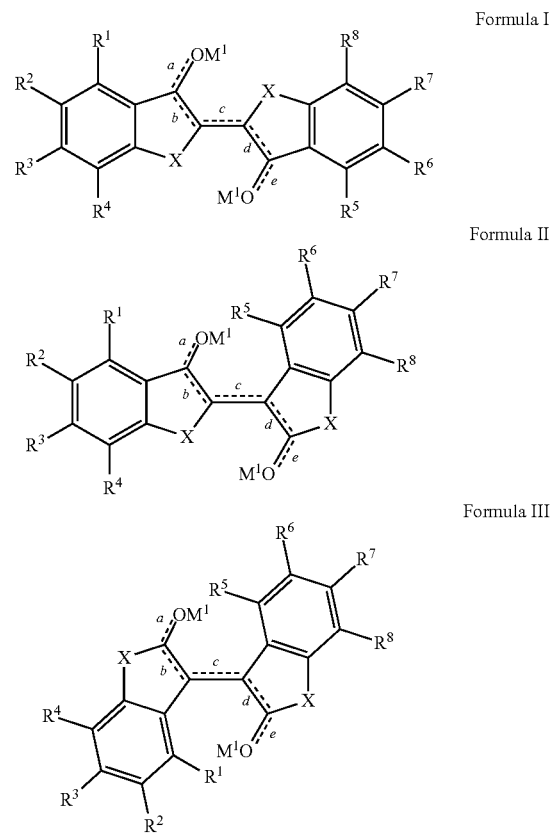

wherein, $R^1$, $R^2$, $R^3$, $R^4$, $R^5$, $R^6$, $R^7$, and R are each independently selected from a hydrogen atom, a group selected from halogen (e.g. F), optionally halogenated alkyl, cycloalkyl, or aryl, —CN, —NO$_2$, —SO$_2$OM$^2$, —OP(O)(OM$^2$)$_2$, —P(O)(OM$^2$)$_2$, Or —C(O)OM$^2$, Wherein M$^2$ is a cation of an alkali or alkaline earth metal, or a —OC(O)alkyl, —SO$_2$NH$_2$, —SO$_2$NHalkyl, or —SO$_2$N(alkyl)$_2$, group;

X is, independently in each occurrence, selected from O, S, NH, NR$^9$, and PH, wherein R$^9$ is selected from natural or synthetic carbohydrate and protective groups, for instance an amine protective group such as trifluoroacetamide, t-butyloxycarbonyl (Boc), benzyloxycarbonyl (Cbz), 9-fluorenylmethyloxycarbonyl (Fmoc), benzyl (Bn), and the like; and i. a, c and e are single bonds, b and d are double bonds, and M$^1$ is H or a cation of an alkali or alkaline earth metal thereby forming a salt with the oxygen atom it is linked to negatively charged (e.g. M$^1$ is Li$^+$, Na$^+$, K$^+$, Ca$^{2+}$, or Mg$^{2+}$) wherein the ratio of cation to the rest of the compound of Formula I provides electroneutrality (e.g. M$^1$ may be Li$^+$ or (Mg$^{2+}$)$_{1/2}$); or ii. a, c and e are double bonds, b and d are single bonds, and M$^1$ is absent; or an oxime thereof (i.e. where =OM$^1$ is replaced with =NOH in Formulae I, II or III), a geometric isomer (e.g. cis or trans) thereof, or a carbohydrate (mono or disaccharide, oligo and polysaccharides, e,g, β-D-glucose or cellulose) complex or conjugate thereof.

In one embodiment, when c is a double bond, this double bond may have a cis or trans geometry. In one embodiment, the c double bond is of trans geometry. In another embodiment, X is NH. In a further embodiment, $R^1$ is identical to $R^5$, and/or $R^2$ is identical to $R^6$, and/or $R^3$ is identical to $R^7$, and/or $R^4$ is identical to $R^8$. In another embodiment, $R^1$ and $R^5$ are both hydrogen and/or $R^2$ and $R^6$ are both hydrogen atoms.

In one embodiment, at least one of $R^1$ to $R^8$ is selected from fluorine, cyano and trifluoromethyl. In another embodiment, $R^1$, $R^4$, $R^5$ and $R^8$ are each hydrogen atoms, and $R^2$, $R^3$, $R^6$ and $R^7$ are as previously defined. In another embodiment, $R^1$, $R^4$, $R^5$ and $R^8$ are each hydrogen atoms, and $R^2$, $R^3$, $R^6$ and $R^7$ are independently selected from fluorine, cyano and trifluoromethyl.

In a further embodiment, $M^1$ is present and is selected from Li, Na and K.

The Indigo blue or derivative (where a, c and e are double bonds) as defined above may also be converted to its reduced form (where b and d are double bonds), for instance, by alkaline reduction. For instance, the reduced form of indigo blue is referred to as Leuco-indigo or indigo white and may be in the form of a salt.

In another example, the compound is a precursor of indigo blue such as a indoxyl-sugar or derivative, reduced form or salt thereof and is a compound of Formula IV:

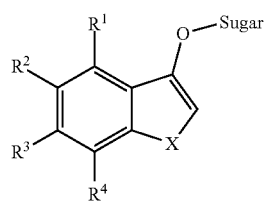

Formula IV wherein, $R^1$, $R^2$, $R^3$, $R^4$, and X are as previously defined; and Sugar is a natural or synthetic carbohydrate (e.g. mono or disaccharide, oligo and polysaccharides, e,g, β-D-glucose or cellulose).

An analog of the compound of Formula IV, where the sugar is replaced with a hydrogen atom is also contemplated.

In one embodiment, the compound used herein is a sugar or polysugar (such as cellulose) complex or conjugate of a compound of Formulae I, II or III.

In one example, the compound is selected from the compounds of the formula:

Compound 1

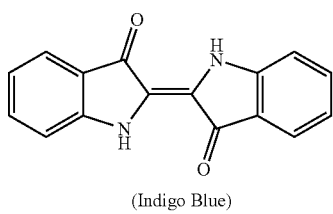

(Indigo Blue)

Compound 2

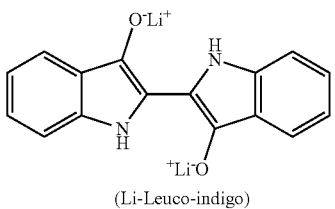

(Li-Leuco-indigo)

Compound 3

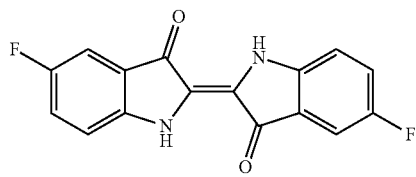

Compound 4

Compound 5

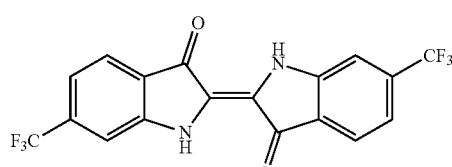

Compound 6

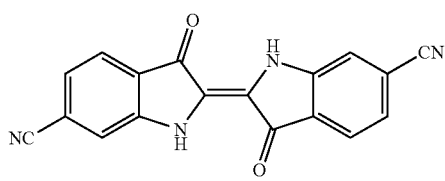

Compound 7

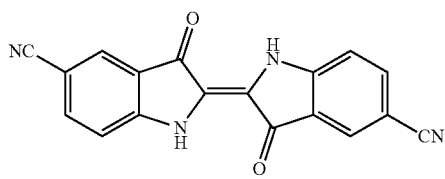

Compound 8

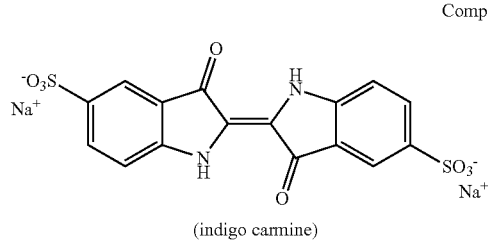

(indigo carmine)

Compound 9

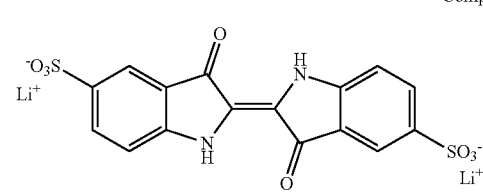

Compound 10

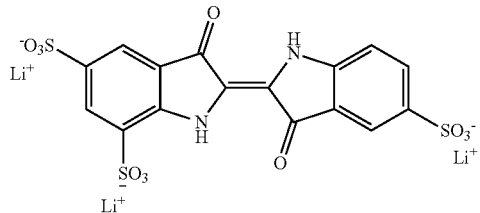

Compound 11

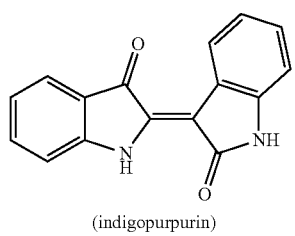

(indigopurpurin)

Compound 12

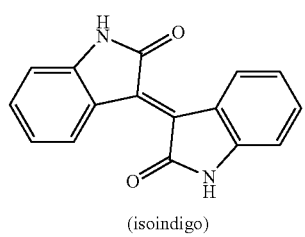

(isoindigo)

Compound 13

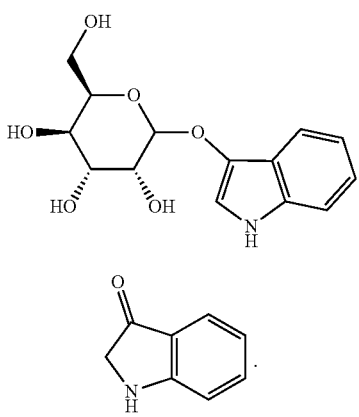

Compound 14

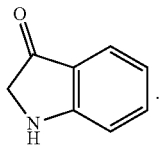

According to some examples, the compound is indigo blue or a derivative thereof having substituents on one or both aromatic rings. For example, one or more sulfonate groups (e.g. indigo carmine), one or more chlorine or bromine atoms (e.g. tyrian purple, ciba blue) or one or more nitrile groups. Other derivatives include the replacement of the amine groups by sulfur atoms in the cycle, i.e. wherein X is S (e.g. thioindigo). In another example, the compound is indigo carmine. In yet another example, the compound is isoindigo. Another example of a compound is indigo purpurine. Another example of an indigoid compound is indolinedione.

Some of the compounds described herein may be available from commercial sources or may be prepared using known techniques, such as those described in Tanoue et al., Dyes and Pigments, 62, 2004, 101-105; Klimovich I. V., J. Mat. Chem., 2014, 2, 7621-7631; Horn, R. H., et al., Notes. Journal of the Chemical Society (Resumed), 1950, 2900-2908; Voß, G. and H. Gerlach, Chemische Berichte, 1989, 122(6), 1199-1201; Baltac, T., et al., Revista de Chimie, 2012, 63(6), 618-620; Bailey, J. E. and J. Travis, Dyes and Pigments, 1985, 6(2), 135-154; Leclerc, S., et al., J. Biol. Chem., 2001, 276(1), 251-260; and Karapetyan G. et al., Chem, Med. Chem., 2011, 6, 25-37, incorporated herein by reference in their entirety for all purposes.

According to another aspect, the present application relates to electrode material comprising a compound as defined herein as an additive. For instance, the compound is present in a concentration from 0.1 wt % to 5 wt %, or in a concentration from 0.1 wt % to 2 wt %, in the electrode material. In one embodiment, the electrode is adapted for use in an electrochemical cell, for instance, in a lithium or lithium-ion battery. In a further embodiment, the electrode is adapted for use in a supercapacitor of the redox type.

In another example, the electrode material comprises a compound as defined herein and particles of an electrochemically active material. In another embodiment, the electrode material comprises a compound as defined herein and particles of an electrochemically active material dispersed in a binder. For instance, the present invention relates to electrodes comprising an electrode material defined herein coated on a support film, e.g. a current collector.

In one embodiment, the electrode is a cathode, for example, of a lithium-ion battery. The present compound may contribute as a capacity reservoir, as an electron conductive agent, as an ion diffusing agent and/or as an overcharge protector. For instance, the presence of a compound described herein may result in increased battery capacity and/or reduced internal resistance, for instance, when operated at low temperature.

Similarly, when the electrode is an anode, for example, of a lithium-ion battery, the present compound may then contribute by increasing electron conductivity and/or ionic diffusion, as an overcharge protector and/or by reducing internal resistance, e.g. at room temperature and below.

For instance, the compound as defined herein may be used to improve ionic and/or electronic conductivity within the electrochemical cell, for instance, when operated at low temperature, e.g. temperatures below room temperature, or ≤25° C., or ≤15° C., or ≤10° C., or ≤0° C., or ≤−10° C., whether it is used as an additive in an anode or an cathode, or in both. For instance, the electrochemical cell is operated at a temperature between −40° C. and 25° C.

Particles of electrochemically active material include inorganic particles such as metal oxides and complex oxides, and carbon particles such as graphite. Examples of electrochemically active materials include, without limitation, titanates and lithium titanates (e.g. $TiO_2$, $Li_2TiO_3$, $Li_4Ti_5O_{12}$, $H_2Ti_5O_{11}$, $H_2Ti_4O_9$, or a combination thereof), lithium and metal phosphates (e.g. $LiM'PO_4$ where M' is Fe, Ni, Mn, Co, or a combination thereof), vanadium oxides (e.g. $LiV_3O_8$, $V_2O_5$, $LiV_2O_5$, and the like), and other lithium and metal oxides such as $LiMn_2O_4$, $LiM''O_2$ (M'' being Mn, Co, Ni, or a combination thereof), $Li(NiM''')O_2$ (M''' being Mn, Co, Al, Fe, Cr, Ti, Zr, and the like, or a combination thereof), or a combination thereof, or any of the above materials further comprising a compatible doping element selected from Groups 2 to 15 of the periodic table of elements. For instance, the active material is selected from lithium iron phosphate (LFP), lithium manganese iron phosphate (LMFP), lithium titanate (LTO), graphite, and lithium nickel manganese cobalt oxide (NMC).

According to another example, the electrochemically active material is of the formula $LiM'PO_4$ wherein M' is Fe, Ni, Mn, Co or a combination thereof optionally doped with a compatible element, for instance optionally doped with an element selected from Mg, Al, B, Ti, V, Cr, Cu, Zn, Mo, Sn, Ca, Sr and W, or a combination thereof. For instance, the electrochemically active material is LiFePO$_4$ or LiMn$_x$Fe$_{1-x}$PO$_4$, where 0<x<1, optionally doped with a compatible element, for instance, optionally doped with an element selected from Co, Ni, Mg, Al, B, Ti, V, Cr, Cu, Zn, Mo, Sn, Ca, Sr and W, or a combination thereof, for instance optionally doped with magnesium. Examples of electrochemically active materials also include compounds of the formula LiM"O$_2$, wherein M" is Mn, Co, Ni, or a combination thereof. For instance, the electrochemically active material is LiNi$_w$Mn$_y$Co$_z$O$_2$, where w+y+z=1.

The electrochemically active material particles are freshly formed or of commercial source. They may be in the form of microparticles or nanoparticles and may further include a carbon coating.

The electrode material optionally includes additional components like conductive materials, inorganic particles, glass or ceramic particles, salts (e.g. lithium salts), and the like. Examples of conductive materials include carbon black, Ketjen™ black, acetylene black, graphite, graphene, carbon fibers, nanofibers (e.g. VGCF) or nanotubes, or a combination thereof.

In one embodiment, the electrode further comprises at least one binder. Examples of binders include water soluble binders such as SBR (styrene butadiene rubber), NBR (butadiene acrylonitrile rubber), HNBR (hydrogenated NBR), CHR (epichlorohydrin rubber), ACM (acrylate rubber), and the like, and cellulose-based binders (e.g. carboxyalkylcellulose, hydroxyalkylcellulose, and combinations), or any combination of two or more of these. For instance, the carboxyalkylcellulose may be carboxymethylcellulose (CMC) or carboxyethylcellulose. Hydroxypropylcellulose is an example of hydroxyalkylcellulose.

Other examples of binders include fluorine-containing polymeric binders such as PVDF and PTFE, and ion-conductive polymer binders such as block copolymers composed of at least one lithium-ion solvating segment and at least one cross-linkable segment.

In one embodiment, the binder comprises a water-soluble binder and a cellulose-based binder, for example, a combination of SBR and CMC.

The present application also relates to the preparation of an electrode comprising the electrode material as defined herein. In one example, a compound as defined herein and particles of an electrochemically active material are mixed with a binder and applied on a substrate film (e.g. a current collector), for instance, as a slurry in a compatible solvent, which may also be selected based on the binder used. For example, water may be used to prepare a slurry with a water-soluble binder and a cellulose-based binder. In another example, a non-aqueous solvent (e.g. NMP) may be used to prepare a slurry with a polymer binder (e.g. a fluorine-containing polymeric binder). Further additives, such as conductive materials may also be added to the slurry. Solvent, if present, is eliminated after coating of the mix or slurry. The binder is as defined above and is selected considering the compatibility with the electrochemically active material, additive, current collector, electrolyte, and other parts of the electrochemical cell which could be in contact therewith.

The slurry can be applied on the substrate film continuously by various methods, such as the comma bar method, the doctor blade method or by slot die casting.

The electrode produced by the present process is for use in the assembly of an electrochemical cell further comprising an electrolyte and a counter-electrode. The material composing the counter-electrode is selected as a function of the electrochemically active material used in the electrode (e.g. electrode/counter-electrode: LFP/LTO, LFP/Li, LFP/Graphite, NMC/Graphite, NMC/LTO, etc.). For instance, the electrode is a positive electrode, and the counter-electrode is a negative electrode and comprises an electrochemically active material selected from metallic lithium, lithium alloys (e.g. Li—Na, Li—Mg, Li—Zn, and the like), Si, SiO$_x$, graphite, and a carbon mixture (graphite-SiO$_x$, graphite-Si, carbon-Si, carbon-SiO$_x$). In another example, the negative electrode comprises a lithium titanate as electrochemically active material (e.g. Li$_4$Ti$_5$O$_{12}$).

The electrolyte may be a liquid, gel or solid polymer electrolyte and, in the case of a lithium or lithium-ion battery, comprises a lithium salt and/or is conductive to lithium ions. For instance, the electrode described herein may be used in capacitors or supercapacitors, or in batteries such as lithium or lithium-ion batteries.

EXAMPLES

The following non-limiting examples are illustrative embodiments and should not be construed as limiting the scope of the present application. These examples will be better understood with reference to the accompanying figures.

Example 1: Chemical Synthesis a) Preparation of 5,5'-Difluoroindigo (Compound 3)

The procedure used here is based on the method described in Tanoue et al., Supra.

Step 1: Preparation of 5-fluoro-3-iodoindole

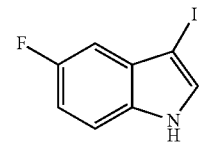 [SMILES: Fc1ccc2[nH]cc(I)c2c1]

To a solution of 5-fluoroindole (100 mg, 0.74 mmol) and sodium hydroxide (29.6 mg, 0.74 mmol) in methanol (10 mL) were added iodine (188 mg, 0.74 mmol) and an aqueous solution (1 mL) of potassium iodide (123 mg, 0.74 mmol). After the mixture was stirred at room temperature for 3 h, water (20 mL) was added. The resulting precipitate was collected by filtration, washed with water, and dried under reduced pressure to obtain 5-fluoro-3-iodoindole (153 mg, 0.584 mmol), which was used for the following reaction without purification.

Step 2: Preparation of 3-acetoxy-5-fluoroindole

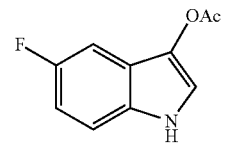 [SMILES: CC(=O)Oc1c[nH]c2ccc(F)cc12]

Silver acetate (146 mg, 0.876 mmol) was added to a solution of 5-fluoro-3-iodoindole from step (a) in acid acetic (10 mL). After stirring for 1 h at 90° C., the mixture was cooled to room temperature and filtered. The filtrate was evaporated to dryness under reduced pressure. The residue was chromatographed on silica gel with chloroform to give 3-acetoxy-5-fluoro-indole (73 mg, 51% yield).

Step 3: Preparation of 5,5'-difluoroindigo

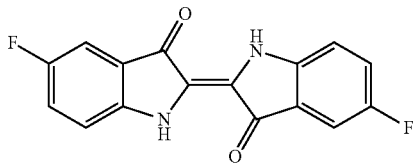 [SMILES: O=C1/C(=C2\Nc3ccc(F)cc3C2=O)Nc2ccc(F)cc21]

To a solution of 3-acetoxy-5-fluoroindole (51 mg, 0.262 mmol) from step (b) in ethanol (5 mL) was added aqueous 1M sodium hydroxide (10 mL). After the mixture was stirred at room temperature for 2 h, water was added. The resulting precipitate was collected by filtration, washed with water, and dried to give 5,5'-difluoroindigo (Compound 3).

This method was also used for the preparation of Compounds 4, 5, 6, and 7 using their corresponding indole as starting material. Other compounds to be used may also be commercially available.

b) General Preparation of Indigo Derivatives

The procedure used here is based on the methods described in Klimovitch, Horn et al., and Voß and Gerlach, Supra.

General Scheme 1

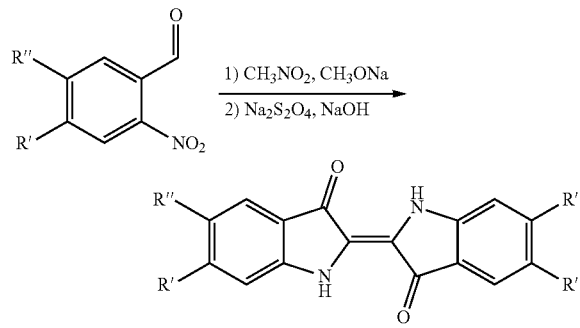

wherein R'=$R^3$ and $R^7$ as defined herein, and R"=$R^2$ and $R^6$ as defined herein.

General Method:

The nitrobenzaldehyde ($3.2 \times 10^{-2}$ mol) derivative and nitromethane (1.1 eq.) in 15 mL of methanol were treated slowly at 0° C. with a solution of sodium methoxide (from sodium (1.2 eq.) and methanol (10 mL)). After 12 h at 0° C., the yellow crystalline sodium salt of 2-nitro-1-o-nitrophenylethylalcohol was collected and washed with ether. This salt was dissolved in water, 15 mL of sodium hydroxide solution (2N) was added, and sodium dithionite (1.1 eq) was then added slowly with stirring. A thick precipitate of indigo was formed at once collected and purified by vacuum-sublimation.

Examples of compounds prepared using this procedure:

| | | |
|---|---|---|
| Compound 3: | R': H | R": F |
| Compound 4: | R': F | R": H |
| Compound 5: | R': $CF_3$ | R": H |
| Compound 6: | R': CN | R": H |
| Compound 7: | R': H | R": CN | c) Preparation of Sulfoindigo

The procedure used below is based on the method described in Batlach et al., Supra.

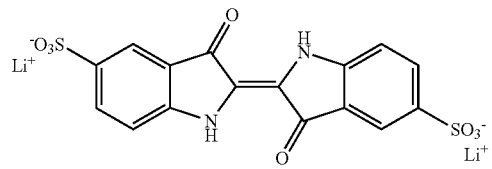

Concentrated sulfuric acid (50 mL) is placed in a 250 mL flask and indigo power (10 g) is added in one portion. The mixture is vigorously stirred during 15 min at 30° C. Then, the solution is heated to 80° C. and it stirred for 2 more hours. It is left until the next day, when an aqueous solution saturated with LiCl is prepared. Ice and then Indigo are added to it and then the solution is filtered. The filtrate is washed with a lithium chloride saturated aqueous solution. The compound may also be prepared as its sodium salt in a similar manner.

d) Preparation of Trisulfoindigo

The following procedure is based on the method described in Bailey and Travis, Supra.

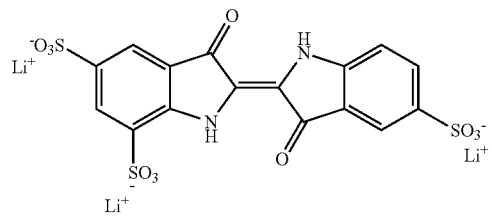

Concentrated sulfuric acid (75 mL) was placed in a 250 mL flask and indigo power (10 g) was added in one portion. An air-cooled condenser was installed, and the mixture was swirled and then heated to 160° C. The reaction was terminated by carefully quenching the solution in 300 g of ice. The resulting solution was neutralized by addition of a 50% LiOH solution (with cooling), refrigerated overnight and then filtered to remove the precipitated solids. The precipitate (mostly 5,5'-diSI) was discarded. The mother liquor was diluted to 900 mL and retained for purification by preparative HPLC. The compound may also be prepared as its sodium salt.

Example 2: Preparation of Exemplary Electrochemical Cells a) Composition of Cathodes:

The composition of cathodes prepared according to (c) below used as reference or tested indigoid-containing cathodes are listed below in Table 1.

TABLE 1

Cathode compositions

| Cathode No | Active Material | Active | C-Black | C-Fibers | PVdF | SBR | CMC | Indigoid[d] |
|---|---|---|---|---|---|---|---|---|
| 1 | LFP[a] | 90 | 5 | — | 5 | — | — | — |
| 2 | LFP[a] | 91 | 5 | — | — | 2.5 | 1.5 | — |
| 3 | LMFP[b] | 90 | 4 | 1 | 5 | — | — | — |
| 4 | LMFP[b] | 90 | 4 | 1 | — | 3.125 | 1.875 | — |
| 5 | NMC[c] | 90 | 5 | — | 5 | — | — | — |
| 6 | NMC[c] | 91 | 5 | — | — | 2.5 | 1.5 | — |
| 7 | LFP[a] | 90 | 5 | — | 4 | — | — | 1 |
| 8 | LFP[a] | 91 | 5 | — | — | 1.875 | 1.125 | 1 |
| 9 | LMFP[b] | 89.5 | 3.75 | 0.75 | 5 | — | — | 1 |
| 10 | LMFP[b] | 89.5 | 3.75 | 0.75 | — | 3.125 | 1.875 | 1 |
| 11 | NMC[c] | 89.5 | 4.5 | — | 5 | — | — | 1 |
| 12 | NMC[c] | 91 | 5 | — | — | 1.125 | 1.875 | 1 |

[a]LFP: LiFePO$_4$ carbon-coated particles, carbon content in LFP being <10% by weight
[b]LMFP: LiMn$_{0.75}$Fe$_{0.25}$PO$_4$ doped with 0.5% Mg, carbon-coated particles, carbon content being <10% by weight
[c]NMC: LiNi$_{0.6}$Mn$_{0.2}$Co$_{0.2}$O$_2$
[d]Indigoid included in cathodes 7 to 12 identified with the letter a: indigo, b: indigo carmine, and
[e]isoindigo (ex: cathode 7-a, 7-b, etc.).

b) Composition of Cells Prepared:

Components of the cells tested are summarized in Table 2 below. Each cell is prepared as a 2032 size coin cell. The separator identified in the table is impregnated with a liquid electrolyte composed of 1 mol/kg LiPF$_6$ in PC/EMC (4/6) or PC/EMC/DMC (4/3/3).

TABLE 2

Cells compositions

| Cell No | Cathode | Separator[a] | Anode[b] | Cell No | Cathode[c] | Separator[a] | Anode[b] |
|---|---|---|---|---|---|---|---|
| A1 | 1 | I | Li | B1 | 7 | I | Li |
| A2 | 2 | I | Li | B2 | 8 | I | Li |
| A3 | 2 | I | Gr | B3 | 8 | I | Gr |
| A4 | 3 | II | Li | B4 | 9 | II | Li |
| A5 | 4 | II | Li | B5 | 10 | II | Li |
| A6 | 5 | I | Li | B6 | 11 | I | Li |
| A7 | 6 | I | Li | B7 | 12 | I | Li |
| A8 | 4 | II | LTO | B8 | 10 | II | LTO |
| A9 | 6 | I | LTO | B9 | 12 | I | LTO |
| A10 | 3 | II | LTO | B10 | 9 | II | LTO |
| A11 | 5 | I | LTO | B11 | 11 | I | LTO |

[a]I: Polyethylene based 16 μm; II: polyethylene and polyethylene terephthalate based 12 μm
[b]Li: lithium metal film; Gr: graphite (commercial); LTO: Li$_4$Ti$_5$O$_{12}$ (LTO): Carbon Black: SBR: CMC in a weight ratio of 91:5:2.5:1.5
[c]Cell name will include cathode letter of Table (ex: cathode 7-a: Cell B1-a, etc.).

c) Methods for the Preparation of Electrodes (See Table 1 Above for Weight Ratios):

LFP+PVDF

The hybrid cathode pastes were prepared by mechanically mixing (Thinky Mixer SR-500) of Indigoid if present (a: indigo, b: indigo carmine, and c: isoindigo, see Table 1), active material, acetylene black (Denka HS-100L) and PVdF (1300 g/mol) in NMP. The resulting viscous slurry was cast by the Doctor Blade method uniformly onto an aluminium foil serving as a current collector, dried at 120° C. under vacuum and roll-pressed with a Rolling Machine (MSK-2150) at 59 μm to achieve an electrode active layer density 8 mg/cm$^2$. Electrodes were further dried under vacuum at 150° C. before to use.

LFP+SBR-CMC

The hybrid cathode pastes were prepared by mechanically mixing (Thinky Mixer SR-500) of Indigoid if present, LFP (LCP 420B), acetylene black (Denka HS-100L), SBR (BM400B) and CMC (BSH-6) in water. The resulting viscous slurry was cast uniformly by the Doctor Blade method onto an aluminium foil serving as a current collector, dried at 80° C. under vacuum and roll-pressed with a Rolling Machine (MSK-2150) at 59 μm to achieve an electrode active layer loading of 8 mg/cm$^2$ and a volume density of 1.8 mg/cm$^3$. The electrodes were further dried under vacuum at 150° C. before to use.

LTO+SBR-CMC

The hybrid cathode pastes were prepared by mechanically mixing (Thinky Mixer SR-500) LTO (T30-D8), acetylene black (Denka HS-100L), SBR (BM400B) and CMC (BSH-6) in water. The resulting viscous slurry was cast uniformly by the Doctor Blade method onto an aluminium foil serving as a current collector, dried at 80° C. under vacuum and roll-pressed with a Rolling Machine (MSK-2150) at 72 μm to achieve an electrode active layer loading of 10 mg/cm$^2$ and a volume density of 1.8 mg/cm$^3$. The electrodes were further dried under vacuum at 150° C. before to use.

LMFP+PVDF

The hybrid cathode pastes were prepared by mechanically mixing (Thinky Mixer SR-500) of Indigoid if present, active material, acetylene black (Denka HS-100L), carbon fiber (VGCF-SDH-HC) and PVdF (1300 g/mol) in NMP. The resulting viscous slurry was cast by the Doctor Blade method uniformly onto an aluminium foil serving as a current collector, dried at 80° C. under vacuum and roll-pressed with a Rolling Machine (MSK-2150) at 63 μm to achieve an electrode active layer density 8.5 mg/cm$^2$. Electrodes were further dried under vacuum at 150° C. before to use.

LMFP+SBR-CMC

The hybrid cathode pastes were prepared by mechanically mixing (Thinky Mixer SR-500) of Indigoid if present, active material, acetylene black (Denka HS-100L), carbon fiber (VGCF-SDH-HC), SBR (BM400B) and CMC (BSH-6) in water. The resulting viscous slurry was cast uniformly by the Doctor Blade method onto an aluminium foil serving as a current collector, dried at 80° C. under vacuum and roll-pressed with a Rolling Machine (MSK-2150) at 63 μm to achieve an electrode active layer loading of 8.5 mg/cm$^2$. The electrodes were further dried under vacuum at 150° C. before to use.

NMC+PVDF

The hybrid cathode pastes were prepared by mechanically mixing (Thinky Mixer SR-500) of Indigoid if present, active material, acetylene black (Denka HS-100L), and PVdF (1300 g/mol) in NMP. The resulting viscous slurry was cast by the Doctor Blade method uniformly onto an aluminium foil serving as a current collector, dried at 80° C. under vacuum and roll-pressed with a Rolling Machine (MSK-2150) at 41 μm to achieve an electrode active layer density 7.5 mg/cm$^2$. Electrodes were further dried under vacuum at 125° C. before to use.

NMC+SBR-CMC

The hybrid cathode pastes were prepared by mechanically mixing (Thinky Mixer SR-500) of Indigoid if present, active material, acetylene black (Denka HS-100L), SBR (BM400B) and CMC (BSH-6) in water. The resulting viscous slurry was cast uniformly by the Doctor Blade method onto an aluminium foil serving as a current collector, dried at 80° C. under vacuum and roll-pressed with a Rolling Machine (MSK-2150) at 41 μm to achieve an electrode active layer loading of 7.5 mg/cm$^2$. The electrodes were further dried under vacuum at 125° C. before to use.

Example 3: Electrochemical Properties a) Redox Properties of Indigoids:

To illustrate the electrochemical properties of the present additives, indigo was included in an electrolyte solution which was tested in half-cells by Linear Scanning Voltammetry (LSV) according to the following conditions (Oxidation vs Al and Reduction VS Cu):

| LSV oxidation | LSV reduction |
|---|---|
| Cells (Al/Li Metal) | Cells (Cu/Li Metal) |
| Aluminium: 15 μm | Cu: 8 μm |
| Cathode cup: Al | Cathode cup: SUS |
| Separator: PE separator (16 microns) | Separator: PE separator (16 microns) |
| Electrolyte: PC/EMC (4/6) 1M LiPF$_6$ | Electrolyte: PC/EMC (4/6) 1M LiPF$_6$ |
| Conditions | Conditions |
| Scan rate: 1 mV/s | Scan rate: 1 mV/s |
| Maximum potential: 7 V vs. Li/Li$^+$ | Maximum potential: OCV |
| Minimum potential: OCV | Minimum potential: 0 V vs. Li/Li$^+$ |
| Repeat: 1 scans | Repeat: 1 scans |

Figure 2:
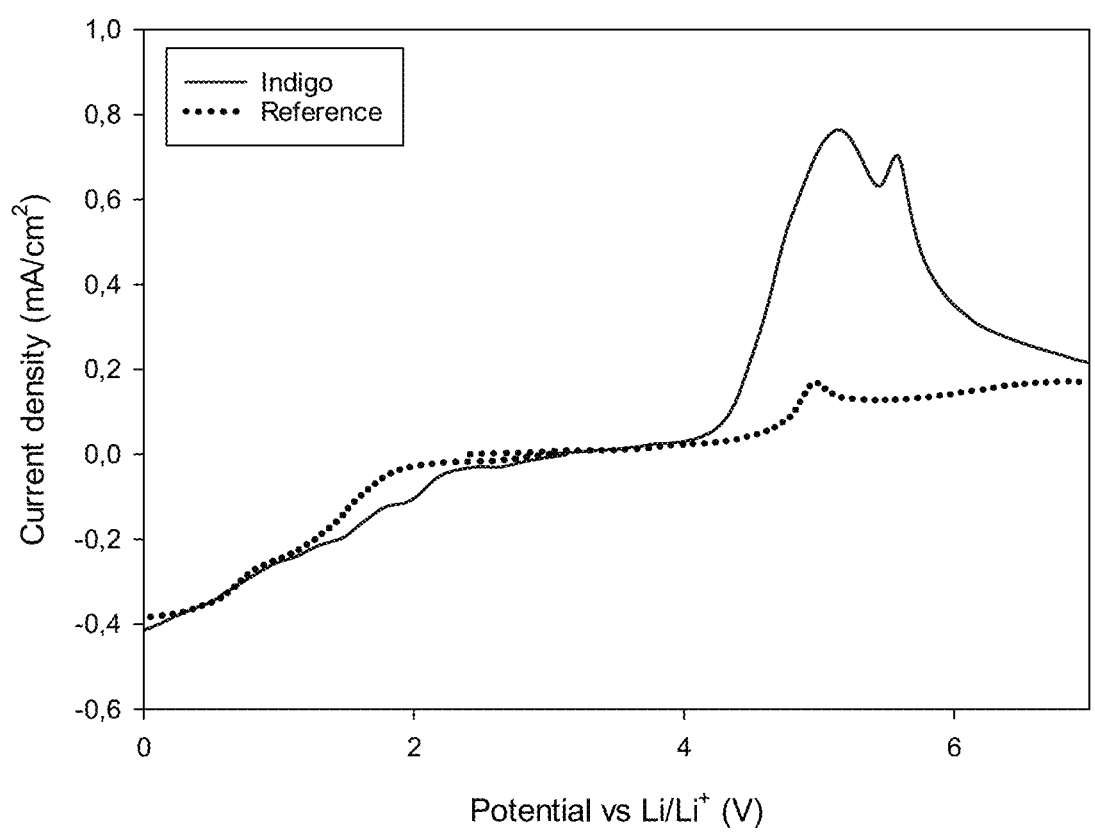
FIG. 2 shows the Linear Scanning Voltammetry (LSV) results for a 1M $LiPF_6$ solution in PC/EMC (4/6) and a 1M $LiPF_6$ solution in PC/EMC (4/6) with 10 mMol indigo (Oxidation vs Al and Reduction vs Cu).
Figure 19:
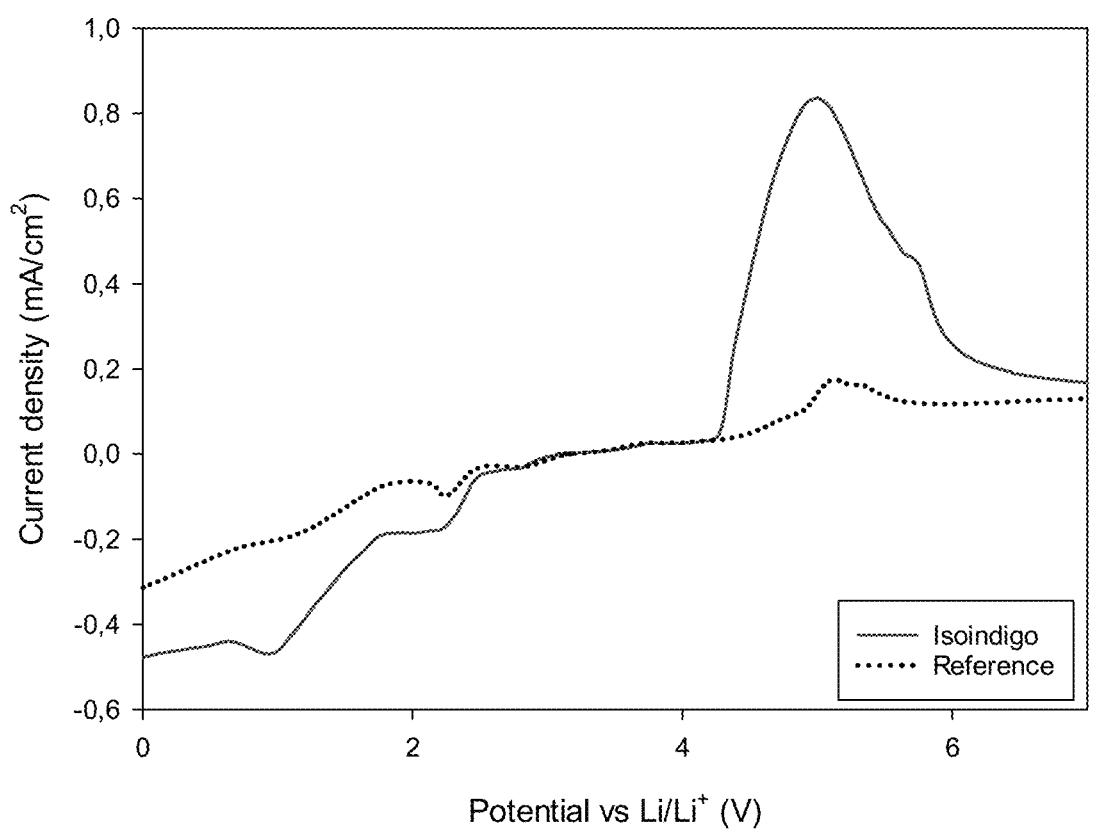
FIG. 19 presents the Linear Scanning Voltammetry (LSV) results for a 1M LiPF$_6$ solution in PC/EMC (4/6) and a 1M LiPF$_6$ solution in PC/EMC (4/6) with 10 mM isoindigo (Oxidation vs Al and Reduction vs Cu).
Figure 24:
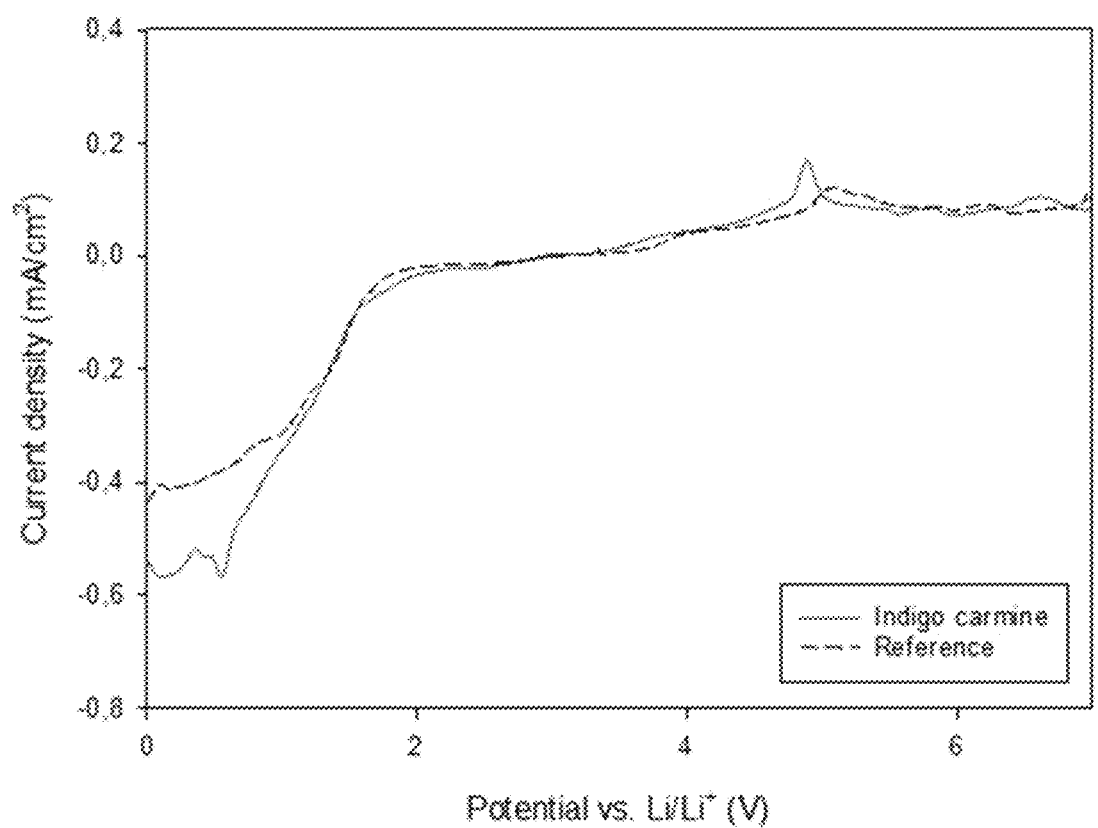
FIG. 24 presents the Linear Scanning Voltammetry (LSV) results for a 1M LiPF$_6$ solution in PC/EMC (4/3/3) and a 1M LiPF$_6$ solution in PC/EMC (4/3/3) with 10 mM indigo carmine (Oxidation vs Al and Reduction vs Cu).

Results are shown in FIG. 2. Oxidation of indigo may be observed after 4V, while the two reduction reactions occur at about 2V and 1.3V. The two reduction reactions are the LFP/LTO electrochemical window while the indigo oxidation would not happen in this system. LSV results are also shown for isoindigo (FIG. 19) and indigo carmine (FIG. 24).

Figure 3:
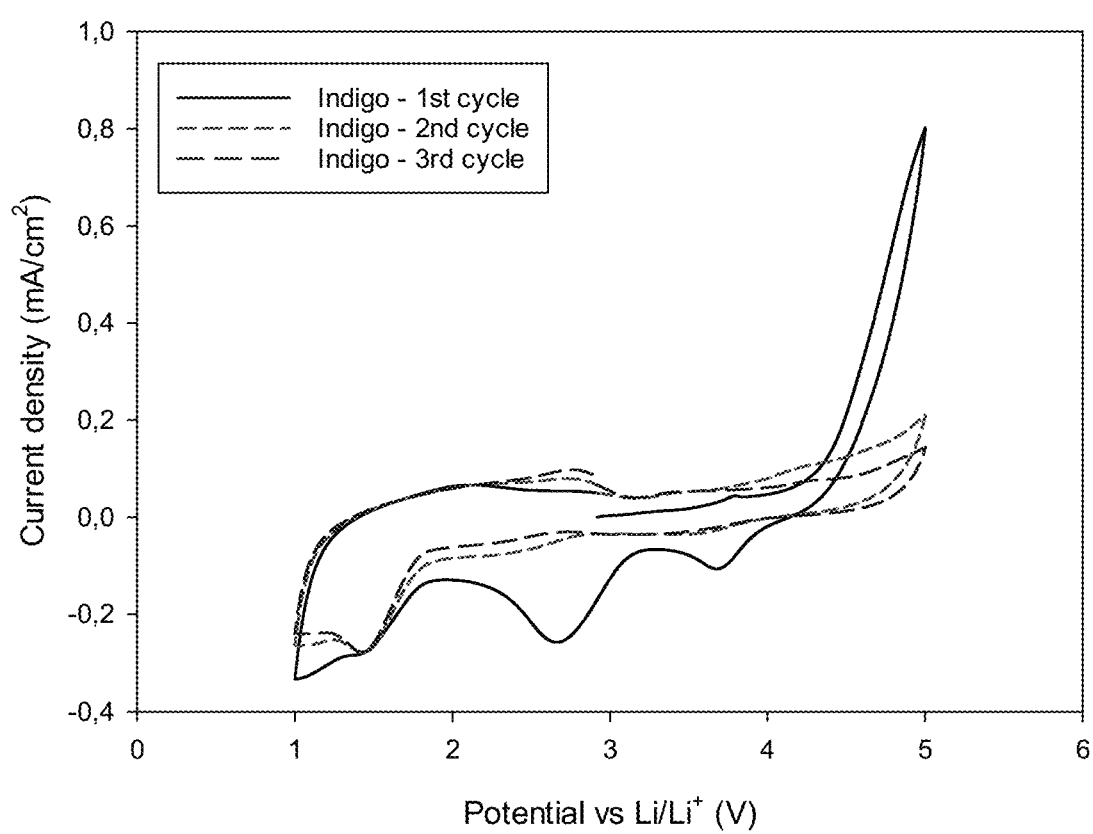
FIG. 3 shows the cyclic voltammetry (CV) results for a 1M $LiPF_6$ solution in PC/EMC (4/6) containing 10 mM indigo.
Figure 18:
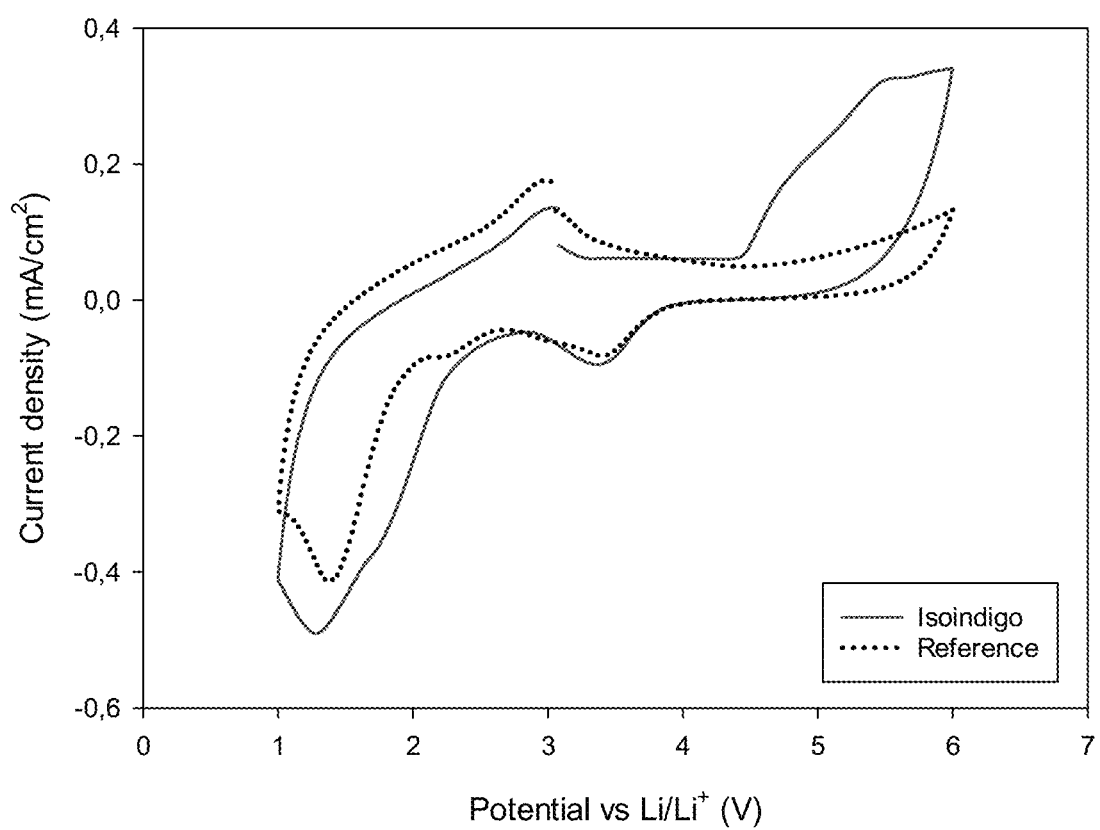
FIG. 18 shows the cyclic voltammetry (CV) results for a 1M LiPF$_6$ solution in PC/EMC (4/6) containing isoindigo (10 mM).
Figure 23:
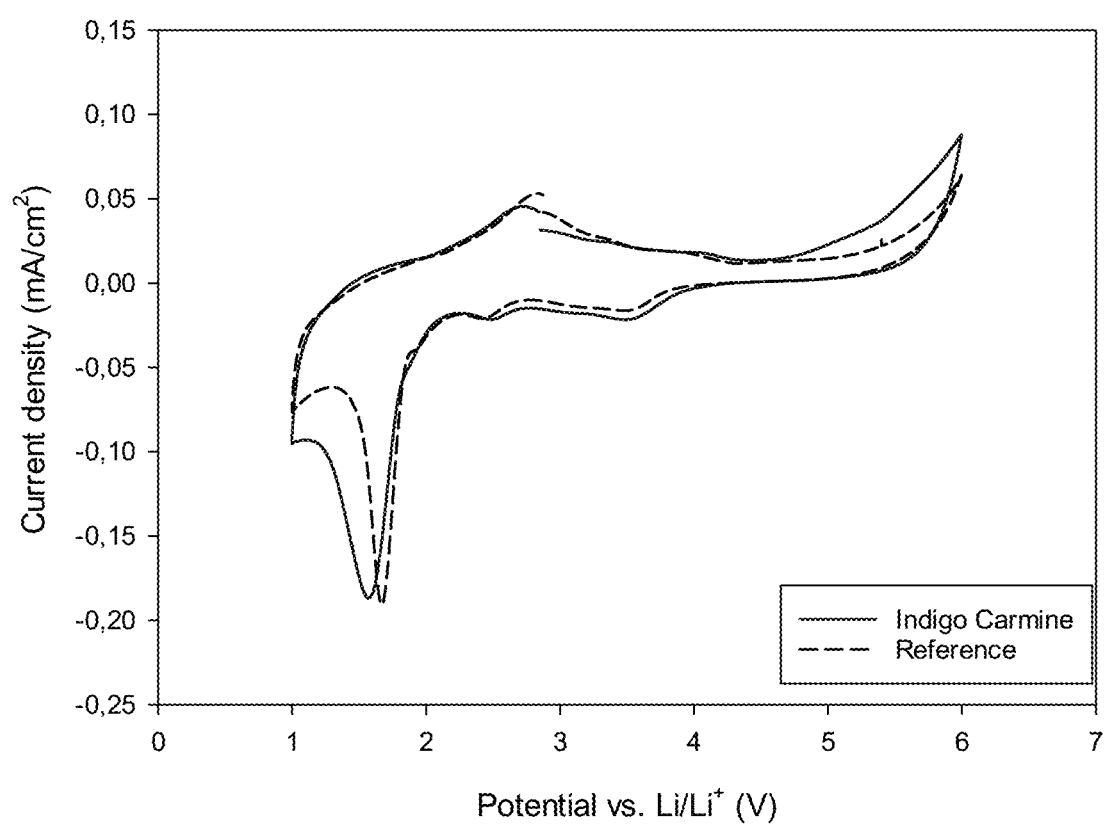
FIG. 23 shows the cyclic voltammetry (CV) results for a 1M LiPF$_6$ solution in PC/EMC/DMC (4/3/3) containing indigo carmine (10 mM).

The same electrochemical solution was also tested by cyclic voltammetry (CV) results for a 1M LiPF$_6$ solution in PC/EMC (4/6) with 10 mMol indigo (same half-cell as for LSV oxidation) at a scan rate of 2 mV/s, a maximum voltage of 6V, a minimum voltage of 1V, and for 3 scans (see FIG. 3). One non-reversible oxidation occurs after 4V and two partially reversible reductions occur in the same analysis conditions. The various oxidation states of indigo are illustrated in FIG. 1. CV results are also presented for isoindigo (FIG. 18) and indigo carmine (FIG. 23).

b) Electrochemical Performance:

Prior to the cycling test, batteries were charged and discharged twice at 0.1 C at 25° C., where xC is the current that can fully charge/discharge cell capacity in 1/x hour. Charge in CC-CV (Constant current constant voltage) mode. Conditions used:

Cells A1, A2, B1, B2 (LFP/Li Metal)
Voltage: 3.8 V Current: 0.2 C
Discharge: CC (Constant current) mode 0.2 C
Cut-off voltage: 2 V Current: 0.01 C
Cells A3 and B3 (LFP/Gr)
Voltage: 3.6 V Current: 0.2 C
Discharge: CC (Constant current) mode 0.2 C
Cut-off voltage: 2 V Current: 0.01 C
Cells A4, A5, B4 and B5 (LMFP-Li)
Voltage: 4.5 V Current: 0.2 C
Discharge: CC (Constant current) mode 0.2 C
Cut-off voltage: 2 V Current: 0.02 C
Cells A6, A7, B6 and B7 (NMC-Li)
Voltage: 4.2 V Current: 0.2 C
Discharge: CC (Constant current) mode 0.2 C
Cut-off voltage: 2.5 V Current: 0.01 C
Cells A8, A10, B8 and B10 (LMFP-LTO)
Voltage: 3 V Current: 0.2 C
Discharge: CC (Constant current) mode 0.2 C
Cut-off voltage: 0.5 V Current: 0.02 C
Cells A9, A11, B9 and B11 (NMC-LTO)
Voltage: 2.7 V Current: 0.2 C
Discharge: CC (Constant current) mode 0.2 C
Cut-off voltage: 0.5 V Current: 0.01 C The results at various temperatures are shown in FIG. 4 (Cells A1 and B1-a) and FIG. 6 (Cells A2 and B2-a).

Figure 4:
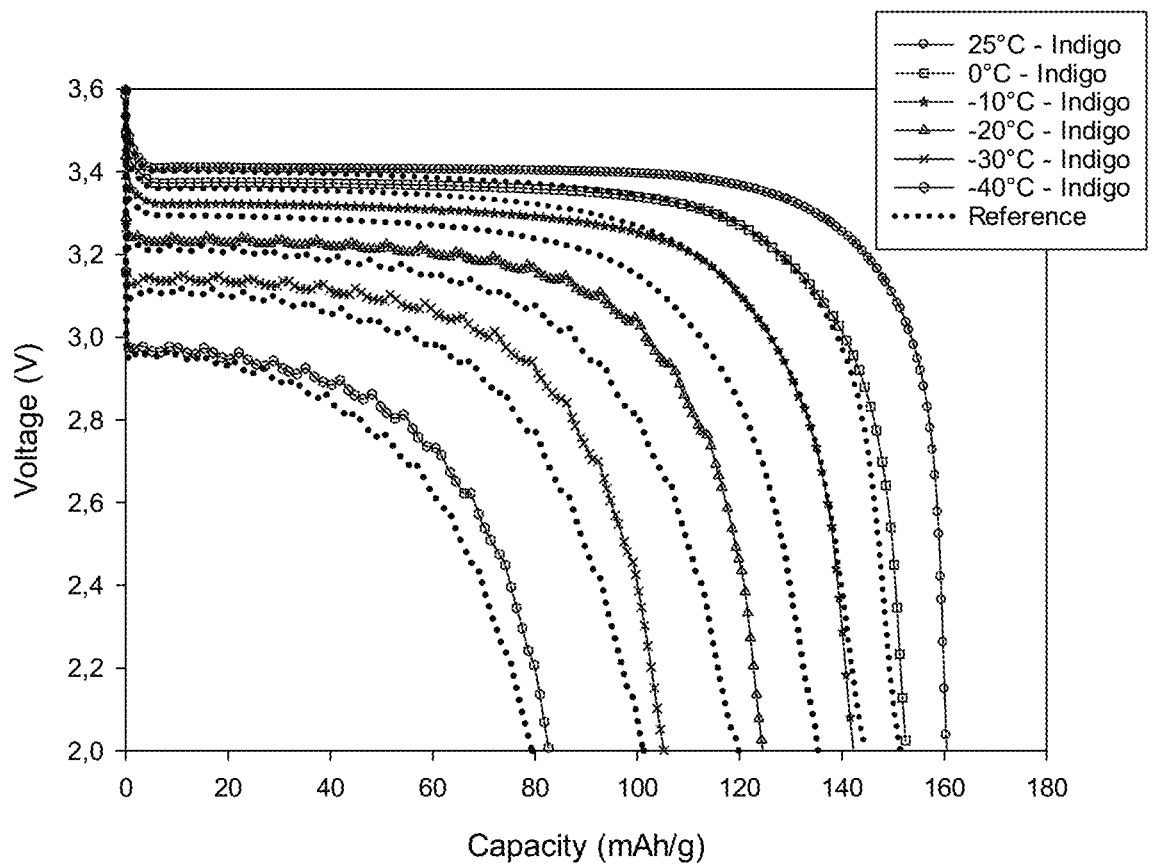
FIG. 4 shows the discharge of LFP/Li and LFP (+1%) Indigo/Li cells using a PVdF binder at temperatures between −40° C. to 25° C.

For instance, FIG. 4 shows the comparative discharge results of LFP/Li and LFP (+1%) Indigo/Li cells (A1 and B1-a respectively) using a PVdF binder at temperatures ranging from −40° C. to 25° C. As can be observed in Table 3 below, the addition of 1% Indigo in LFP provides an increase in capacity of between 4 and 6% between −40 and 25° C.

TABLE 3

Capacity of Cells A1 and B1-a at varying temperatures

| Temperature (° C.) | −40 | −30 | −20 | −10 | 0 | 25 |
|---|---|---|---|---|---|---|
| Cell A1 | 79.41 | 101.18 | 119.8 | 135.32 | 144.45 | 151.4 |
| Cell B1-a | 82.61 | 104.78 | 124.41 | 141.99 | 152.44 | 160.47 |
| % | 4 | 3.6 | 3.85 | 4.93 | 5.53 | 6 |

Figure 6:
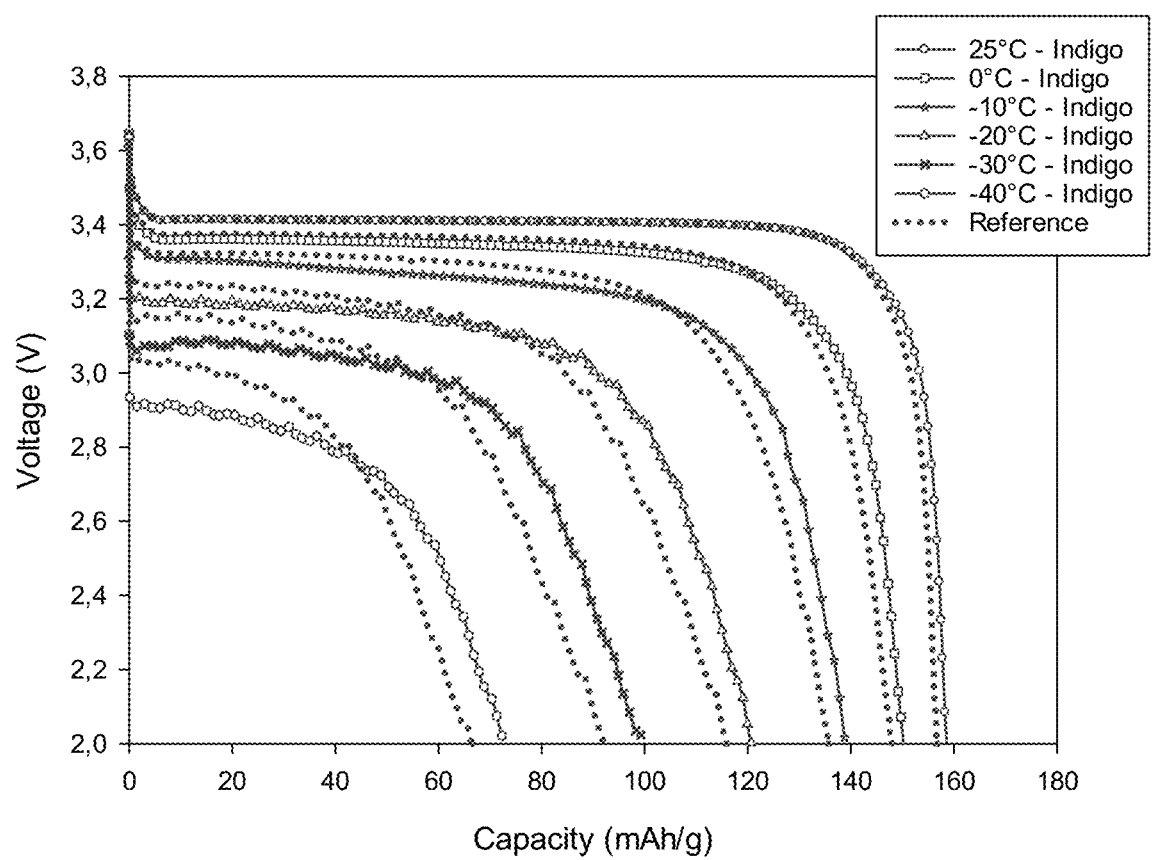
FIG. 6 shows discharge results for LFP/Li and LFP (+1%) Indigo/Li cells using a SBR-CMC binder and 1M $LiPF_6$ solution in PC/EMC (4/6) at temperatures between −40° C. to 25° C.

The discharge results for LFP/Li and LFP (+1%) Indigo/Li cells (A2 and B2-a respectively) using a SBR-CMC binder at temperatures between −40° C. to 25° C. are shown in FIG. 6. Table 4 shows that a 1% addition of Indigo in the LFP cathode provides an increase in capacity between 1 and 10% at temperatures from −40 to 25° C.

TABLE 4

Capacity of Cells A2 and B2-a at varying temperatures

| Temperature (° C.) | −40 | −30 | −20 | −10 | 0 | 25 |
|---|---|---|---|---|---|---|
| Cell A2 | 66.51 | 92.18 | 115.34 | 135.32 | 147.51 | 156.62 |
| Cell B2-a | 72.73 | 99.77 | 120.65 | 138.6 | 149.98 | 158.53 |
| % | 9.35 | 8.22 | 4.6 | 2.4 | 1.7 | 1.2 |

Tables 5(a) to 5(c) below summarize capacities and efficiencies of various indigoids tested using a PVdF or SBR-CMC binder. Impedance results in view of the reference cells (without indigoid) are also presented.

TABLE 5(a)

| | LFP-Li | | | | | |
|---|---|---|---|---|---|---|
| | Capacity (mAh/g) | | Efficiency (%) | | Impedance vs Ref | |
| | PVDF | SBR/CMC | PVDF | SBR/CMC | PVDF | SBR/CMC |
| Compound 1 | 162 | 168 | 99 | 98 | >> | < |
| Compound 8 | 169 | 162 | 100 | 99 | >> | >> |
| Compound 11 | — | 161 | — | 94 | — | < |
| Compound 12 | 165 | 159 | 99 | 98 | < | >> |
| Compound 14 | 164 | 163 | 96 | 99 | >> | >> |
| Reference | 160 | 163 | 99 | 97 | — | — |

TABLE 5(b)

| | NMC-Li | | | | | |
|---|---|---|---|---|---|---|
| | Capacity (mAh/g) | | Efficiency (%) | | Impedance vs Ref | |
| | PVDF | SBR/CMC | PVDF | SBR/CMC | PVDF | SBR/CMC |
| Compound 1 | 165 | 166 | 93 | 99 | > | << |
| Compound 8 | — | 158 | — | 99 | — | < |
| Compound 11 | — | — | — | — | — | — |

TABLE 5(b)-continued

| | NMC-Li | | | | | |
|---|---|---|---|---|---|---|
| | Capacity (mAh/g) | | Efficiency (%) | | Impedance vs Ref | |
| | PVDF | SBR/CMC | PVDF | SBR/CMC | PVDF | SBR/CMC |
| Compound 12 | — | 165 | — | 96 | — | << |
| Compound 14 | — | 162 | — | 100 | — | > |
| Reference | 165 | 161 | 95 | 98 | — | — |

TABLE 5(c)

| | LMFP-Li | | | | | |
|---|---|---|---|---|---|---|
| | Capacity (mAh/g) | | Efficiency (%) | | Impedance vs Ref | |
| | PVDF | SBR/CMC | PVDF | SBR/CMC | PVDF | SBR/CMC |
| Compound 1 | 158 | 156 | 99 | 98 | > | < |
| Compound 8 | 160 | — | 99 | — | > | — |
| Compound 11 | — | — | — | — | — | — |
| Compound 12 | 161 | — | 99 | — | < | — |
| Compound 14 | 160 | — | 100 | — | > | — |
| Reference | 158 | 158 | 99 | 97 | — | — |

Cycling data are also presented in Table 6 below, which summarizes retention rate as well as efficiency of a Cell B1-a compared to a Cell A1. It can be observed that the lithium cell containing LFP and indigo as an additive exhibit a reduced capacity loss. It was also observed that the indigo-containing cell had a more stable efficiency.

TABLE 6

| | Indigo | | Reference | |
|---|---|---|---|---|
| No cycles | Retention | Efficiency | Retention | Efficiency |
| 1 | 99 | 96 | 99 | 99 |
| 21 | 95 | 98 | 95 | 98 |
| 25 | 93 | 97 | 79 | 98 |
| 30 | 90 | 95 | 65 | 86 |
| 50 | 53 | 94 | 27 | 94 |

Figure 13:
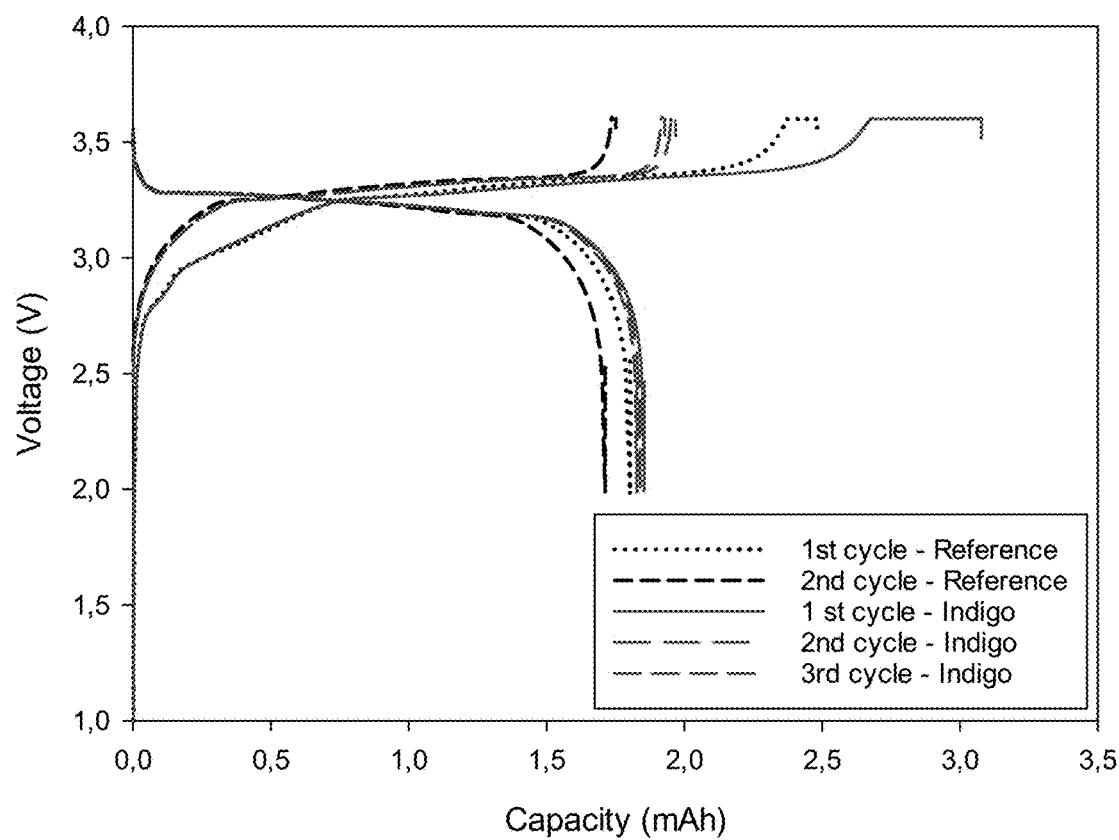
FIG. 13 presents charge-discharge results for LFP/Gr and LFP (+1%) Indigo/Gr cells using a SBR-CMC binder and 1M LiPF$_6$ solution in PC/EMC (4/6).

Cells including graphite as anode material were also tested. The charge discharge results for Cells A3 and B3-a are shown in FIG. 13. A marked irreversibility can be observed at the first cycle in the presence of indigo. After the first cycle, the battery stabilizes more rapidly than for a battery without an indigoid additive. An improvement in capacity and a reduction in impedance are also observed in the presence of indigo (see below). Impedance results are also presented in FIG. 14 for the LFP/Graphite cell with and without indigo (Cells A3 and B3-a).

Figure 15:
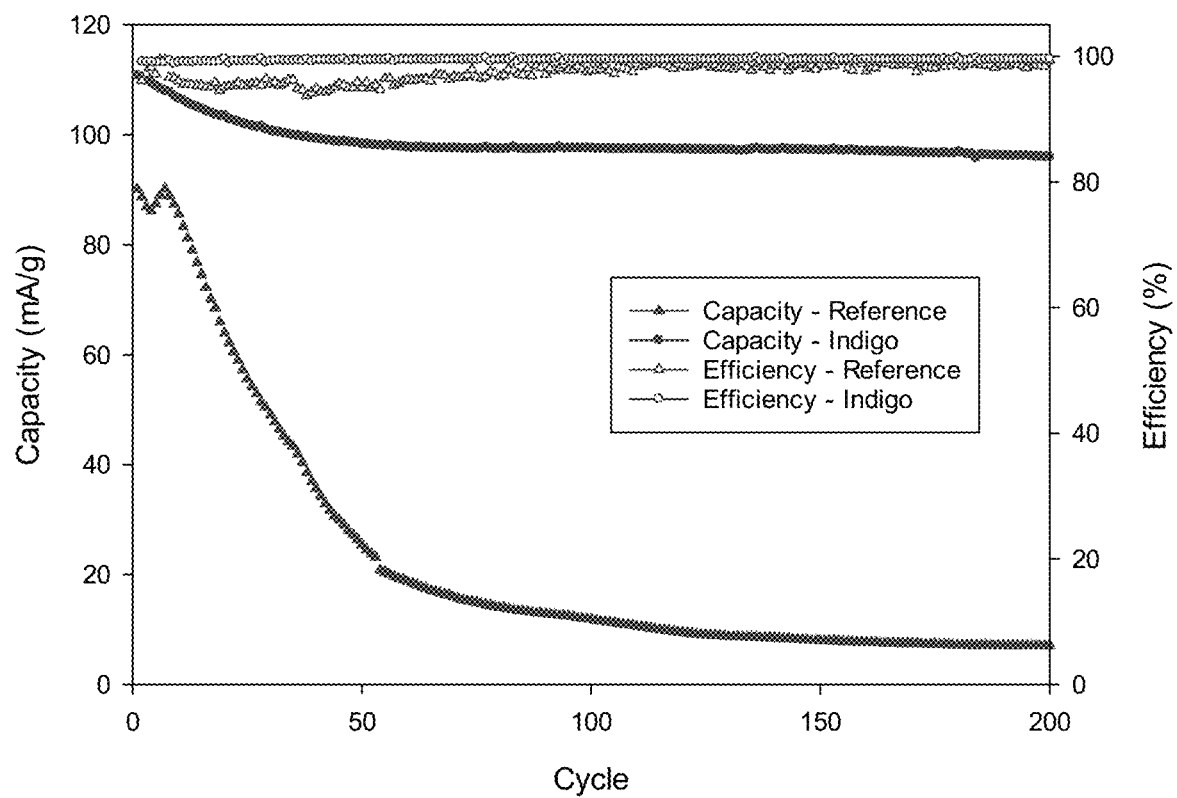
FIG. 15 presents the cycling data (capacity and efficiency) for NMC/Li and NMC(1% indigo)/Li cells using SBR-CMC as binder and 1M LiPF$_6$ solution in PC/EMC (4/6) as electrolyte.
Figure 16:
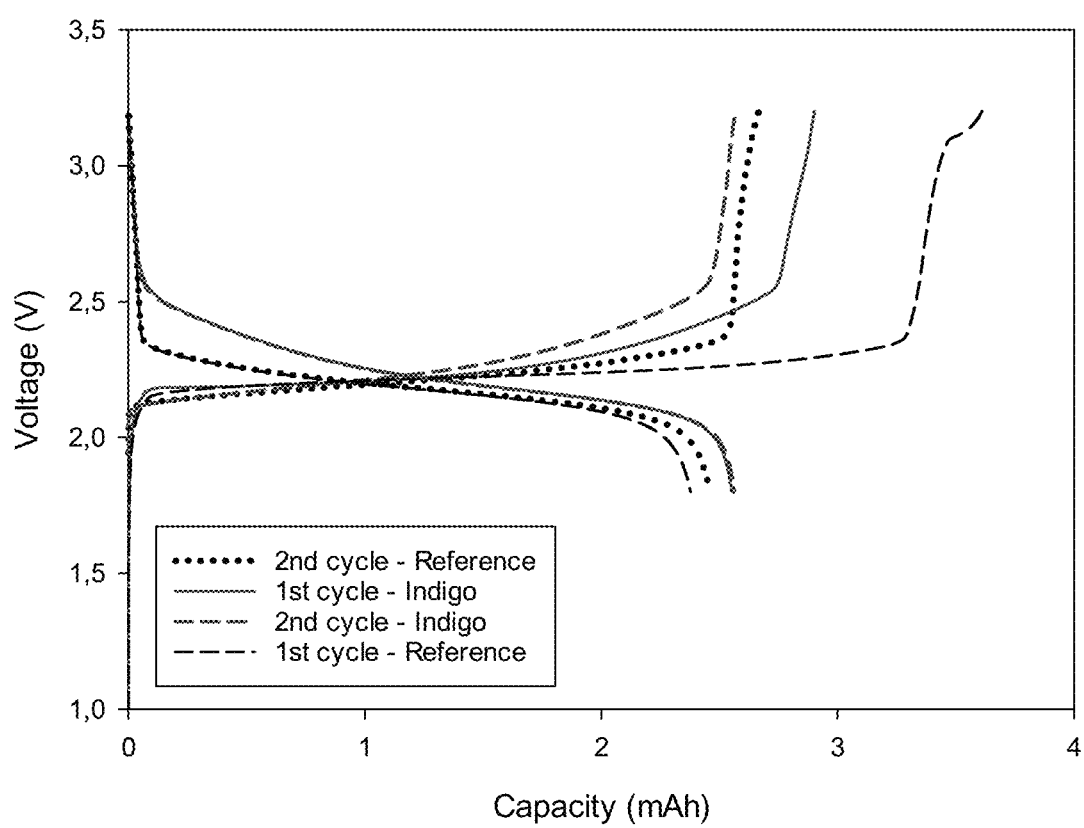
FIG. 16 shows charge-discharge results for NMC/LTO and NMC (+1%) Indigo/LTO cells using a SBR-CMC binder and 1M LiPF$_6$ solution in PC/EMC (4/6).

Cells A7 and B7-a, where the cathode material used was NMC (6/2/2). Cycling results are shown in FIG. 15. It is worth noting that it is normally very difficult to obtain a NMC-Li battery with cycling capabilities. As can be observed from FIG. 15, nearly all capacity is lost after 50 cycles (see reference). On the other hand, when indigo is used as an additive in the NMC cathode, a stable capacity as well as a stable efficiency are obtained over 200 cycles. Charge and discharge results are also shown for NMC/LTO cells A9 and B9-a in FIG. 16.

Figure 20:
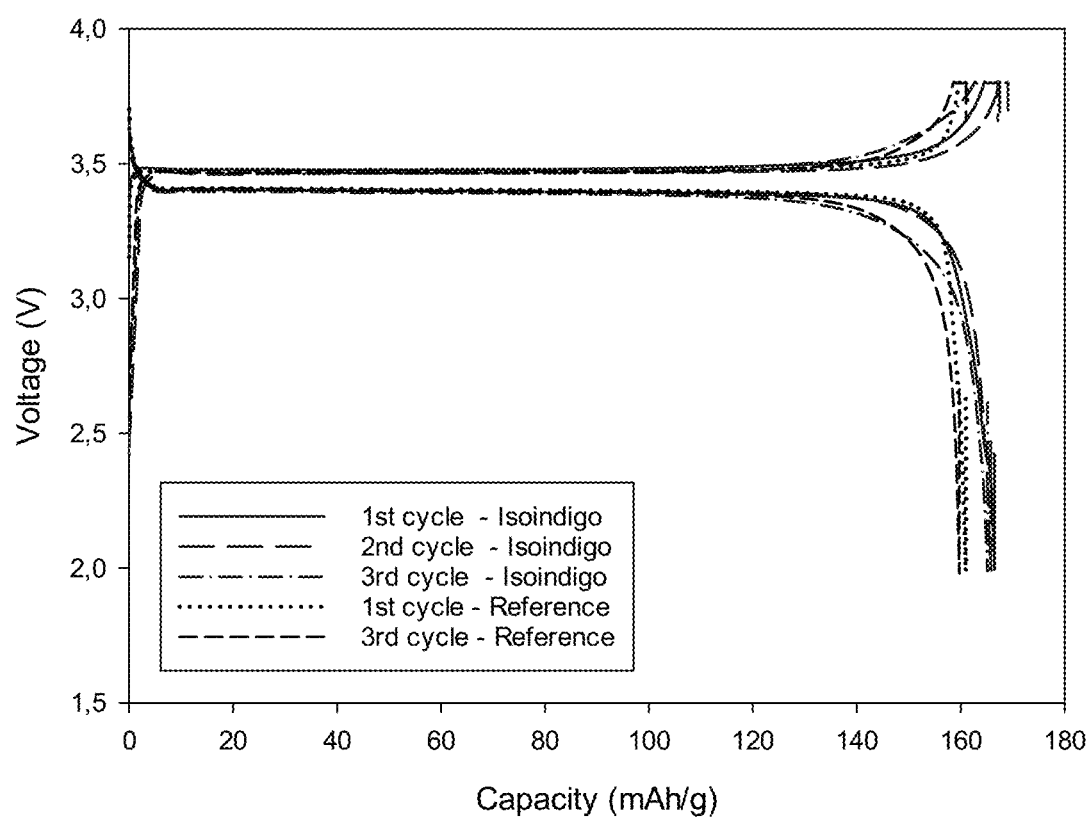
FIG. 20 presents charge-discharge results for LFP/Li and LFP (+1%) isoindigo/Li cells using PVdF as binder and 1M LiPF$_6$ solution in PC/EMC/DMC (4/3/3).
Figure 21:
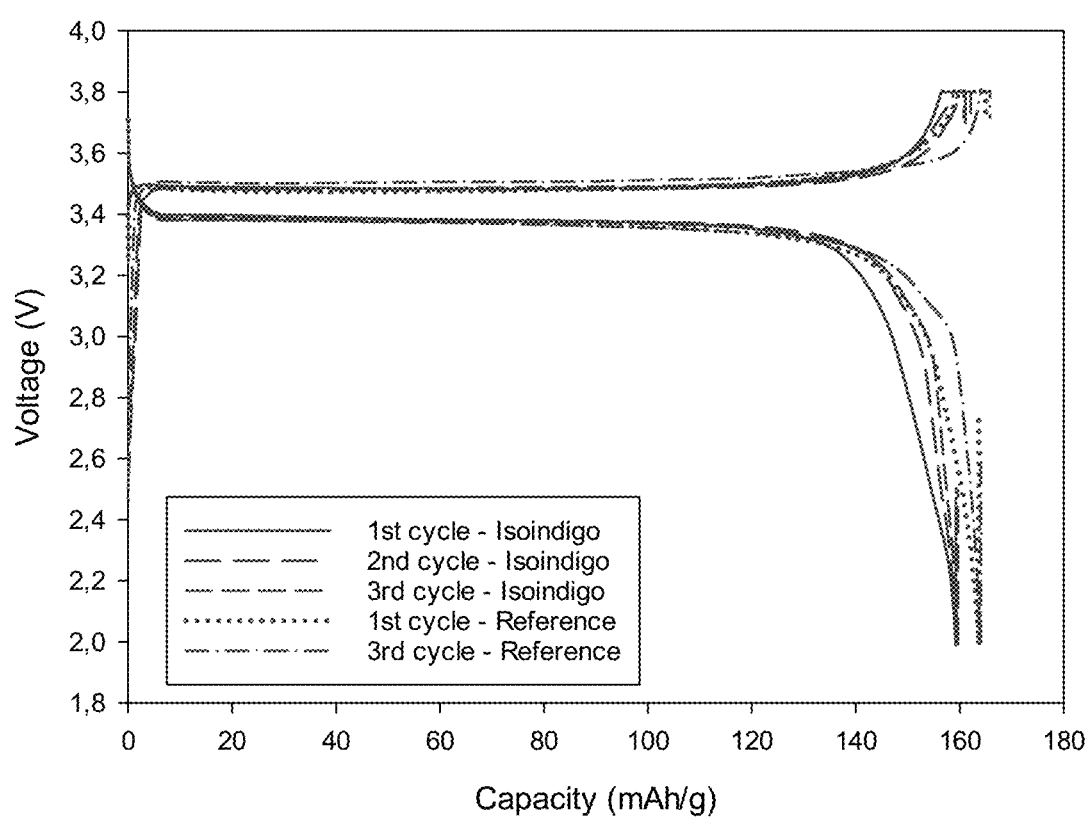
FIG. 21 presents charge-discharge results for LFP/Li and LFP (+1%) isoindigo/Li cells using SBR-CMC as binder and 1M LiPF$_6$ solution in PC/EMC (4/6).

Charge-discharge results are shown for LFP-Li cells A1 and B1-c with or without isoindigo in FIG. 20 (PVDF binder) and for LFP-Li cells A2 and B2-c with or without isoindigo in FIG. 21 (SBR-CMC binder).

Figure 25:
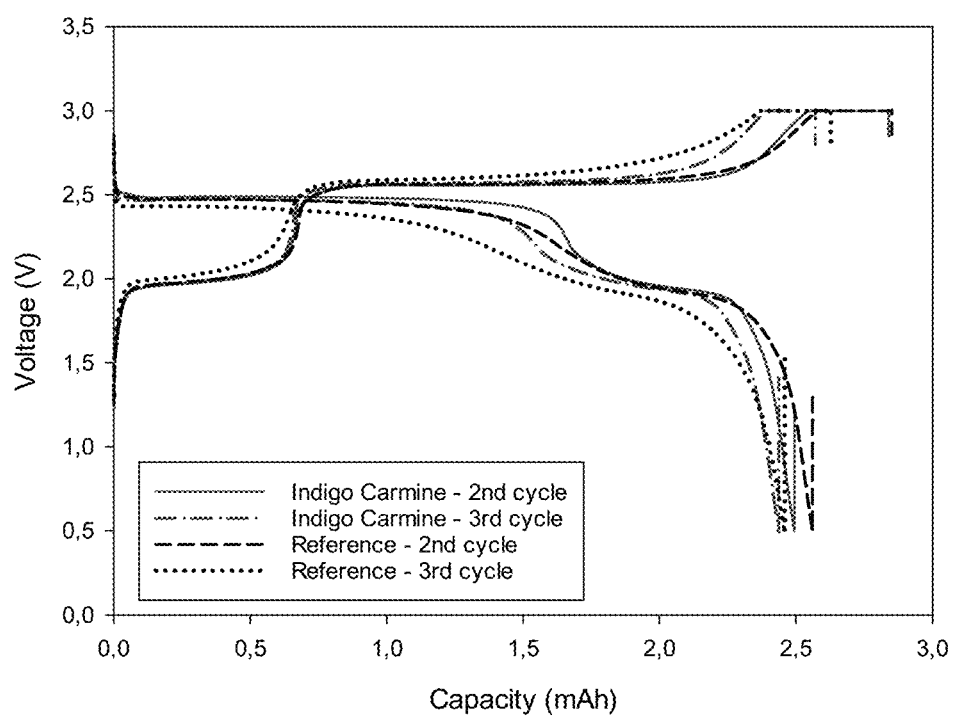
FIG. 25 shows the charge-discharge results of LMFP/LTO and LMFP (+1%) indigo carmine/LTO cells using SBR-CMC as binder and 1M LiPF$_6$ solution in PC/EMC/DMC (4/3/3).

Finally, charge discharge results are presented in FIG. 25, for Cells A8 and B8-b using indigo carmine as additive in a LMFP cathode when using LTO as anode material. The addition of indigo carmine in the cathode material was shown to limit the voltage fading typically observed with LMFP.

c) Electrochemical Impedance:

Electrochemical impedance spectroscopy (EIS) was also performed using LFP-Li Cells A1, A2, B1-a and B2-a described in Example 2 at SOC 50% at various temperatures ranging from −40° C. to 25° C. The frequencies used were 1 MHz-10 mHz, and 1 MHz-50 mHz at low temperature. AC amplitude was 10 mV. The results are shown in FIGS. 5 (a) and 5 (b) for Cells A1 and B1-a, while FIGS. 7(a) and 7(b) show the results obtained with Cells A2 and B2-a.

Figure 5:
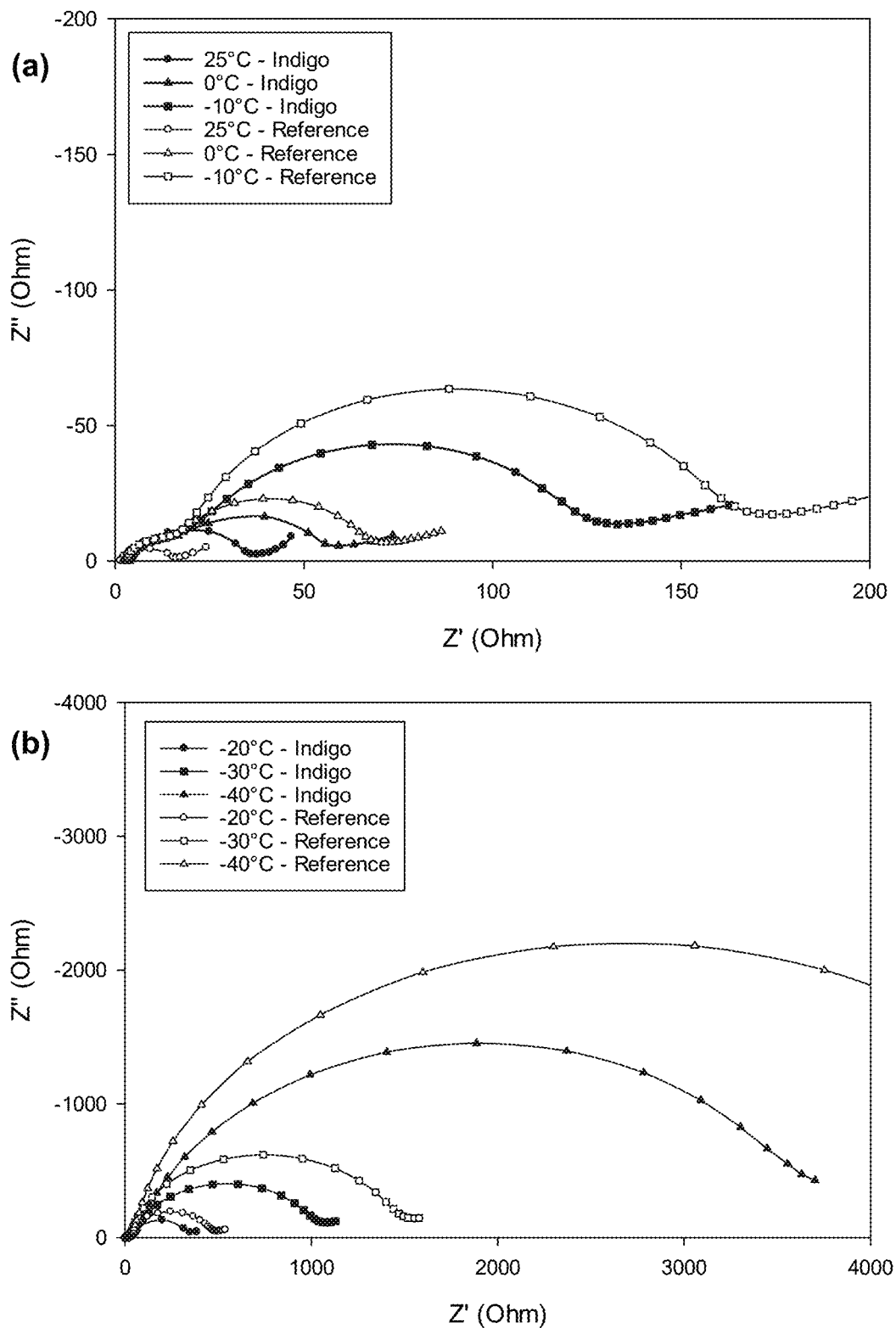
FIG. 5 shows the impedance results for LFP/Li and LFP (+1%) Indigo/Li with PVdF as a binder at: (a) 25° C., 0° C., and −10° C.; and (b) −20° C., −30° C., and −40° C.

FIG. 5 shows the impedance results for LFP/Li and LFP (1% indigo)/Li with PVdF as binder (Cells A1 and B1-a). In curves showing two half circles, one represents the resistance related to lithium while the other is linked to the LFP resistance. The results show that resistance due to LFP decreases with the presence of indigo at temperatures of 0° C. and below.

Figure 7:
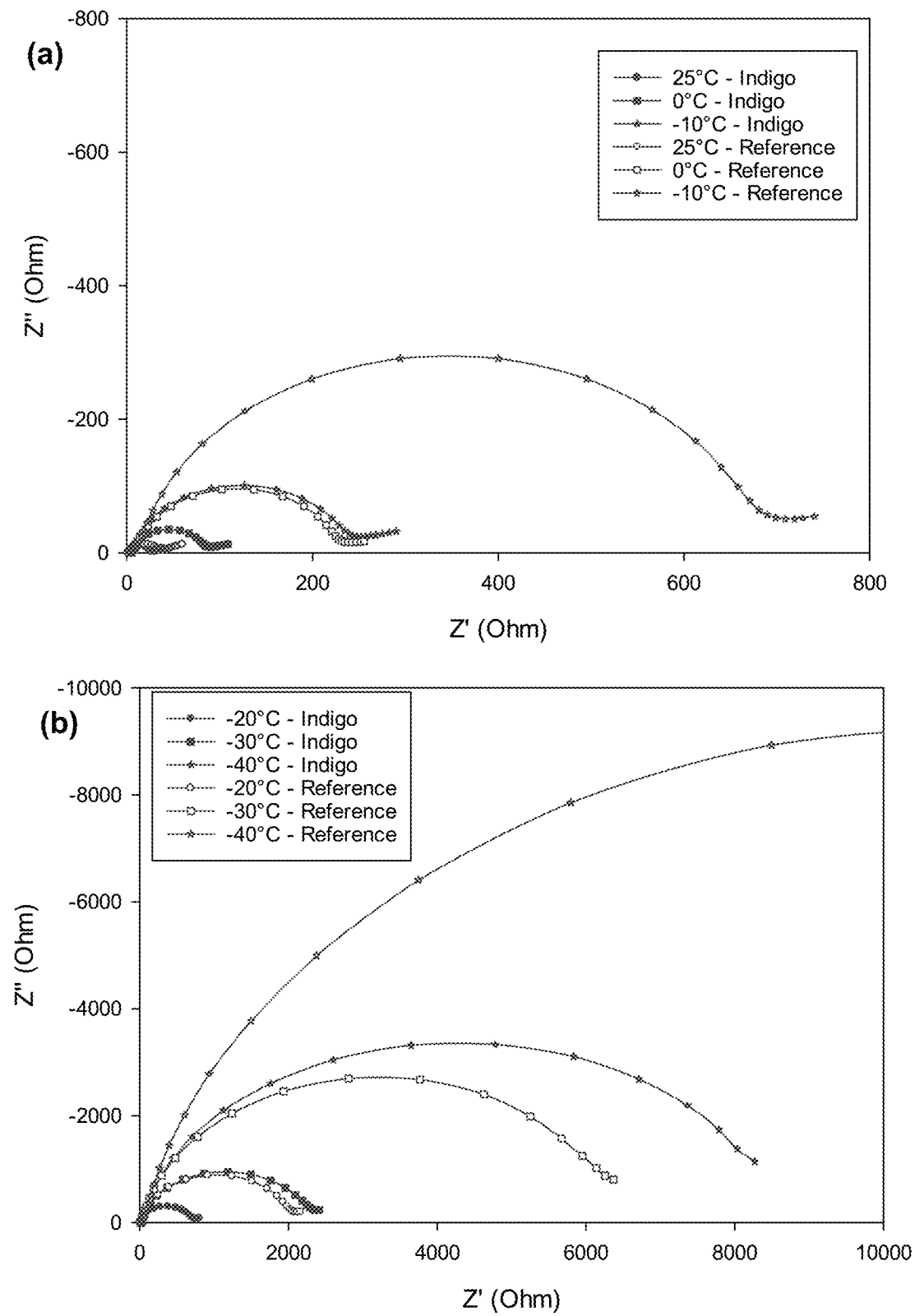
FIG. 7 shows the impedance results for LFP/Li and LFP (+1%) Indigo/Li with SBR-CMC as a binder at: (a) 25° C., 0° C., and −10° C.; and (b) −20° C., −30° C., and −40° C.

Similar impedance results are presented in FIG. 7 for LFP/Li and LFP (1% indigo)/Li with SBR-CMC as a binder (Cells A2 and B2-a). The results show that resistance due to LFP decreases with the presence of indigo at all temperatures tested.

Figure 8:
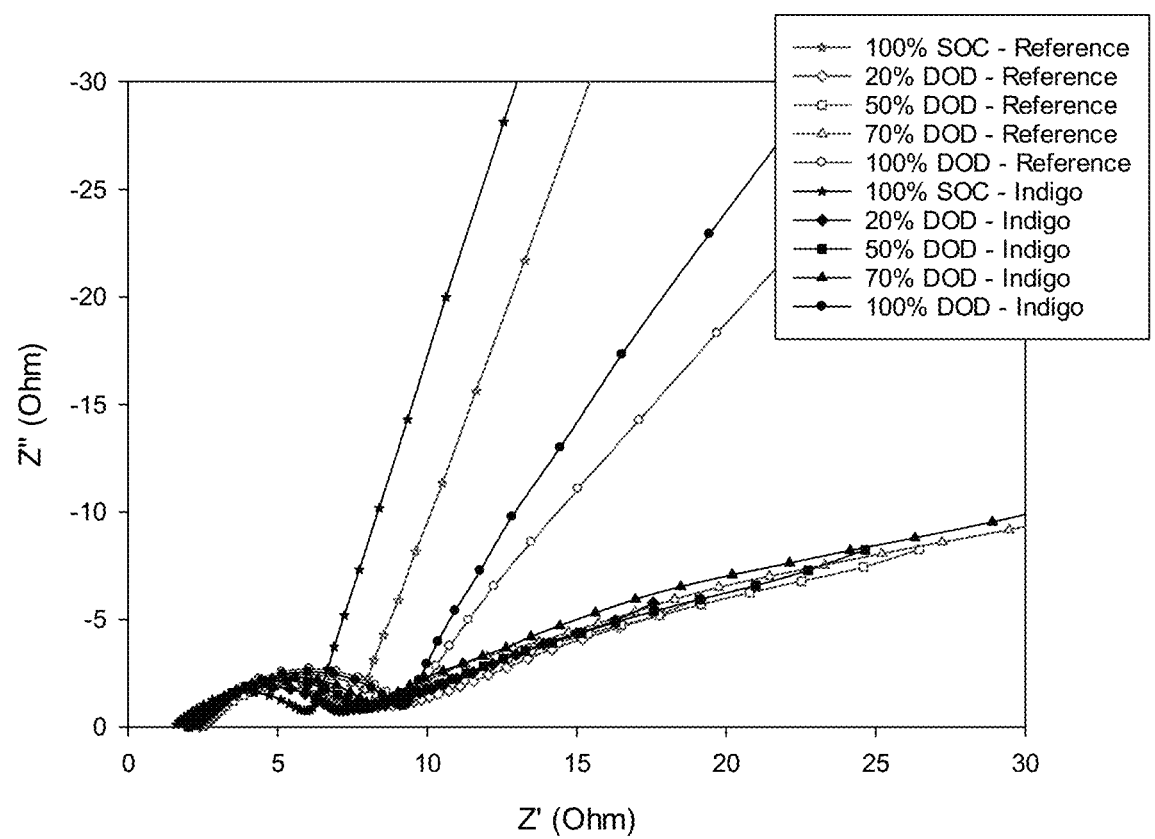
FIG. 8 shows impedance results at 25° C. for LFP/Li and LFP (+1%) Indigo/Li with SBR-CMC as a binder at different % SOC or % DOD.

Impedance of Cells A2 and B2-a at 25° C. was also tested at different state of charge (% SOC). FIG. 8 shows these impedance results. In summary, this experiment serves to demonstrate that the diffusion of lithium ions is improved in LFP with the presence of indigo during charge and discharge, especially at 100% or 80% SOC.

Figure 14:
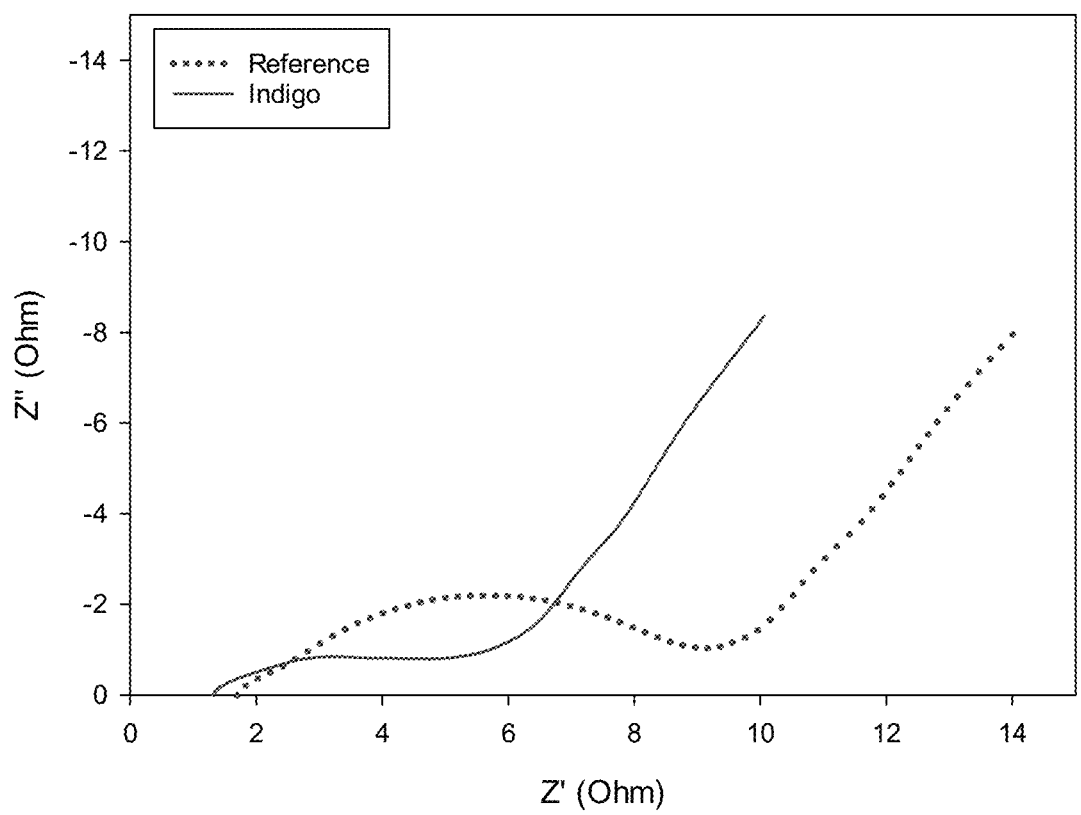
FIG. 14 shows impedance results for LFP/Gr and LFP (+1%) Indigo/Gr with SBR-CMC as a binder.

Impedance results are also presented in FIG. 14 for the LFP/Graphite cell with and without indigo (Cells A3 and B3-a). A reduction of impedance was also observed in the presence of indigo when graphite was used as the anode.

Figure 17:
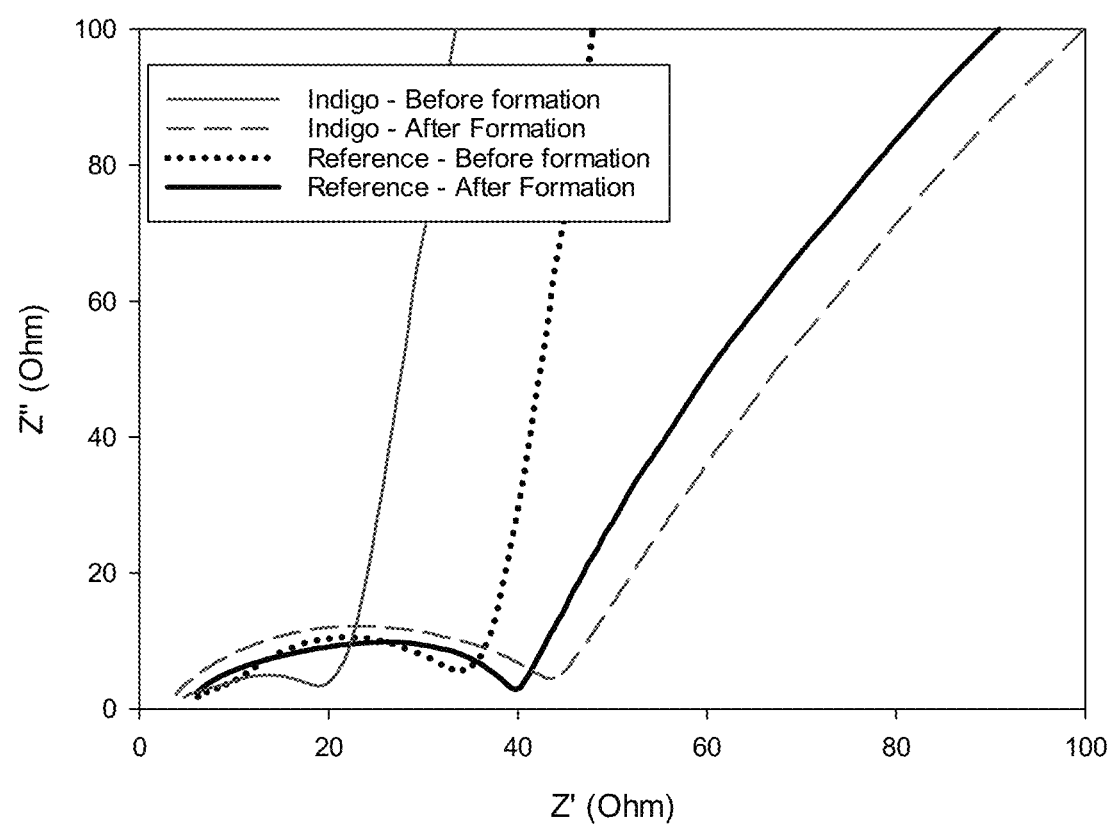
FIG. 17 shows the impedance results for NMC/LTO and NMC (+1%) Indigo/LTO cells with SBR-CMC as a binder.
Figure 22:
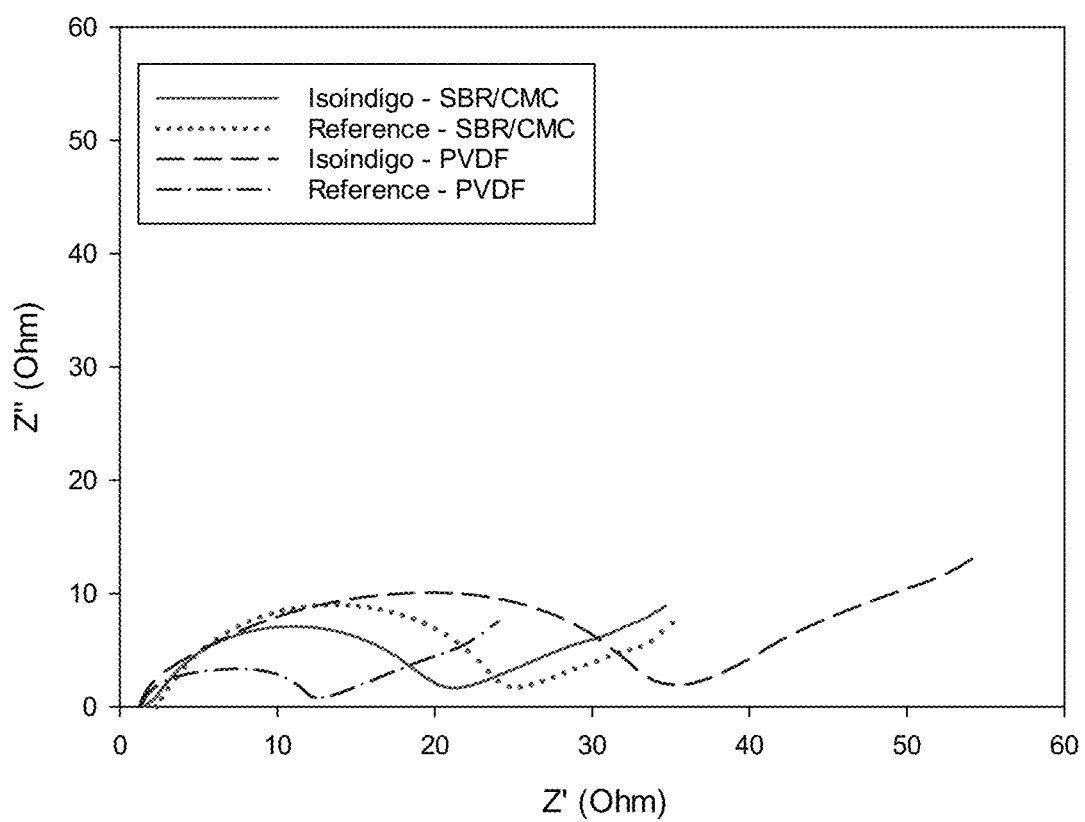
FIG. 22 shows the impedance results for LFP/Li and LFP (+1%) isoindigo/Li cells using PVdF as binder and 1M LiPF$_6$ solution in PC/EMC/DMC (4/3/3), and for LFP/Li and LFP (+1%) Isoindigo/Li cells using SBR-CMC as binder and 1M LiPF$_6$ solution in PC/EMC (4/6).

FIG. 17 shows the impedance results of NMC/LTO Cells A9 and B9-a, where a slight increase was observed. FIG. 22 presents the impedance results for Cells A1, A2, B1-c and B2-c using isoindigo as additive. The reduction in impedance is observed while SBR-CMC is used in combination with isoindigo.

Figure 26:
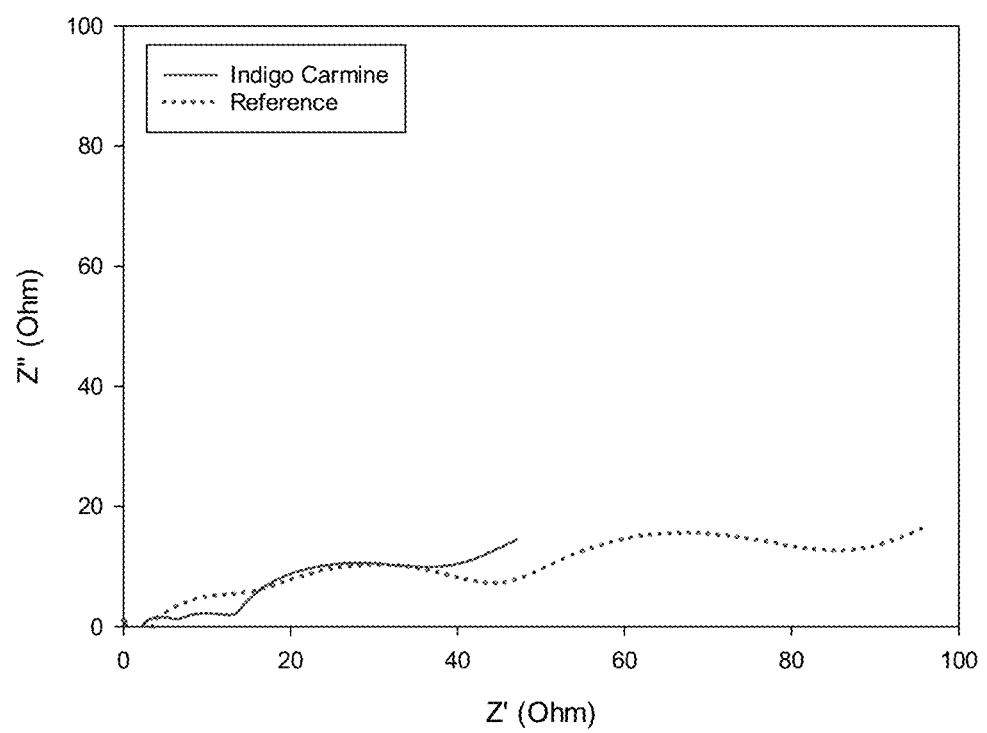
FIG. 26 presents the impedance results for LMFP/LTO and LMFP (+1%) indigo carmine/LTO cells using SBR-CMC as binder and 1M LiPF$_6$ solution in PC/EMC/DMC (4/3/3).

Finally, impedance results are presented in FIG. 26, for Cells A8 and B8-b using indigo carmine as additive in a LMFP cathode when using LTO as anode material. The addition of indigo carmine in the cathode material was shown to greatly reduce the internal battery resistance.

Figure 10:
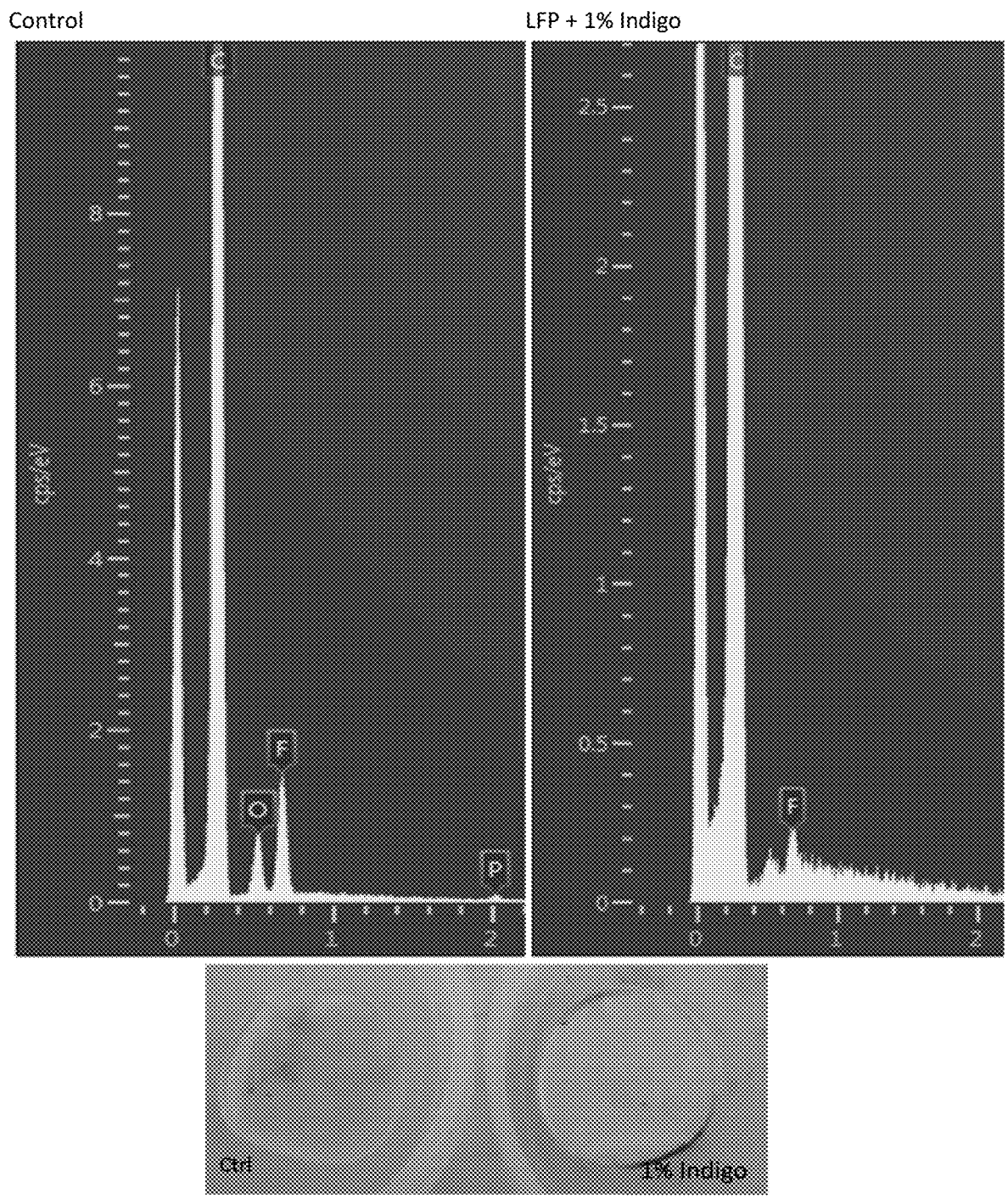
FIG. 10 shows results of energy-dispersive X-ray spectroscopy of the surface of the separators after cycling without indigo (left) and with indigo (right) in LFP/Li cells with SBR-CMC as binder (photos of separators shown underneath the graphs).
Figure 12:
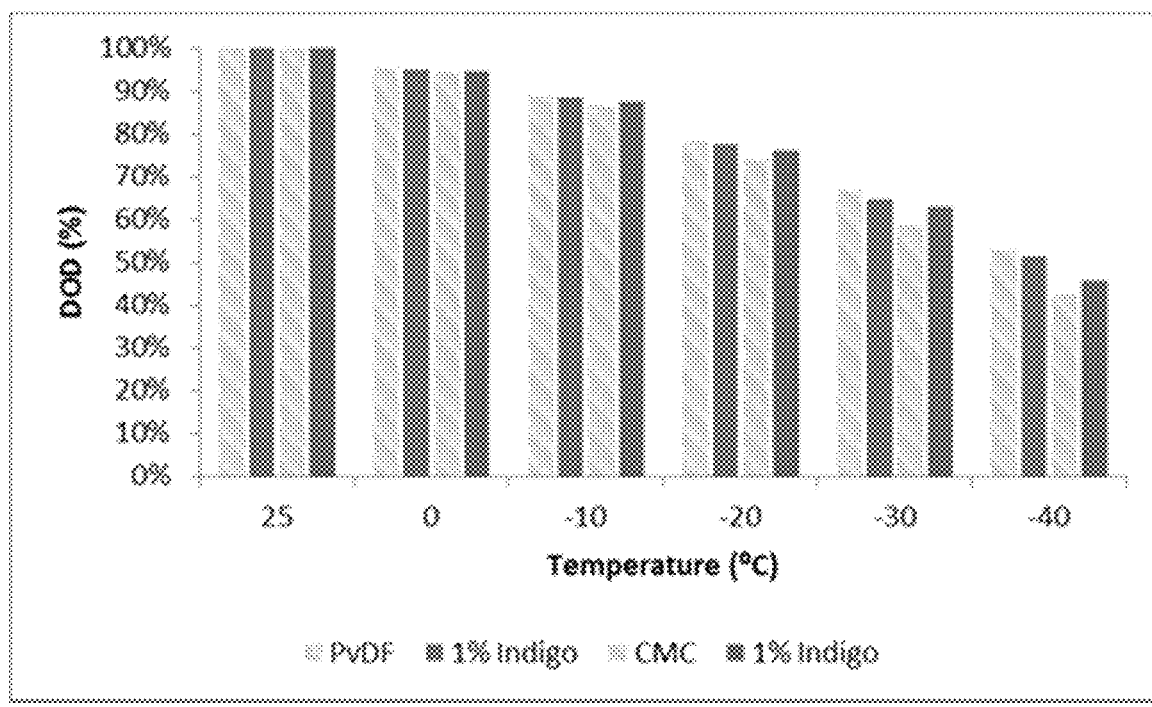
FIG. 12 shows the DOD (%) results as a function of the binder used with 1% or without Indigo.

As can be observed, the presence of an indigoid generally reduces cell impedance, compared to its indigo-free version when tested at the same temperature. This improvement is true for both binders but particularly significant when SBR: CMC is used as binder.

d) Depth of Discharge:

The depth of discharge (% DOD) was evaluated as a function of temperature, binder and presence or absence of indigo for four cells, appearing in FIG. 12 in the following order: Cell Al, Cell B1-a, Cell A2, and Cell B2-a. These comparative results show that the depth of discharge is improved at low temperature in the presence of indigo in LFP especially when combined with the use of CMC-SBR as a binder.

e) Electrolyte Stability:

Cells A2 and B2-a were opened after cycling for a visual evaluation of the separator (see FIG. 10, underneath the graphs). Traces of impurities were observed on the surface of the separator in contact with the LFP cathode in the cell not containing indigo (left-hand image), while such impurities were not present when indigo was used as an additive (right-hand image).

Figure 9:
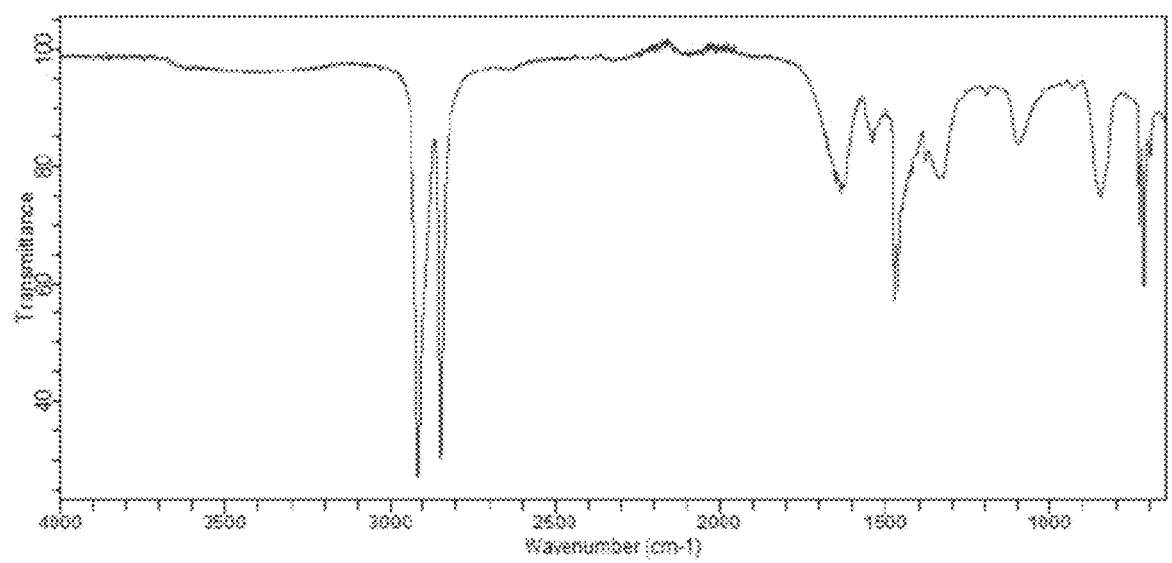
FIG. 9 shows the Fourier transform infrared (FTIR) spectra of the separator after cycling of an LFP/Li cell (a) without the use of indigo and (b) in the presence of 1% indigo.
Figure 9:
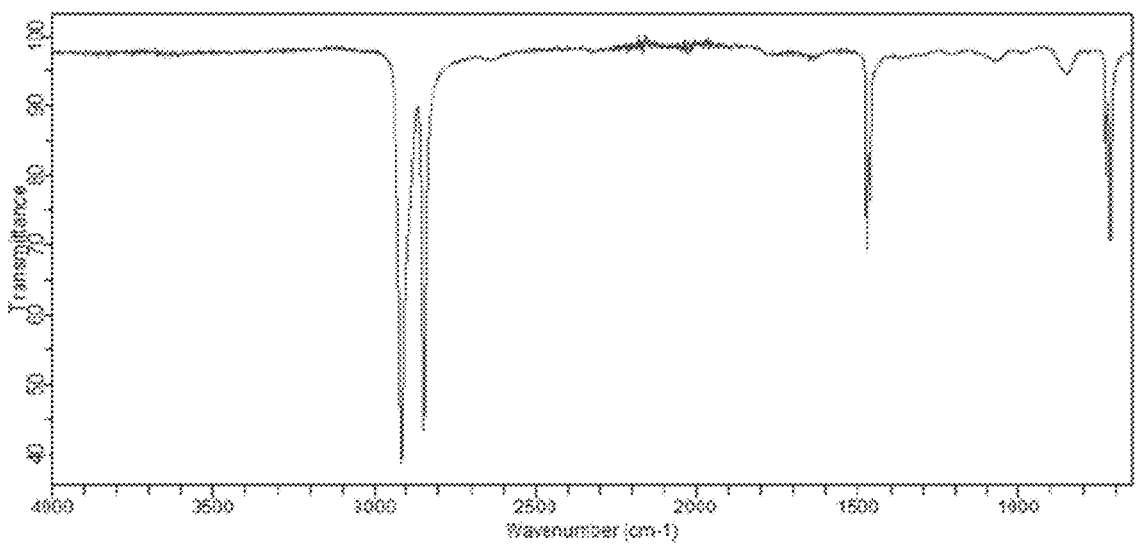

The separator of both cells was then analysed by Fourier transform infrared (FTIR) spectra. FIG. 9(a) shows the FTIR of Cell A2 separator. Peaks observed below 2000 cm$^1$ are typical of electrolyte solvents (carbonates) degradation products. On the other hand, no such peaks linked to the degradation of the electrolyte were observed in FIG. 9(b) showing the FTIR spectra of the separator after cycling in the presence of 1% indigo.

EDS results shown in FIG. 10 also demonstrate that the separator of a LFP-Li cell after cycling without indigo (left) presents a much higher content in F and P atoms at its surface than the corresponding cell with indigo (right). These impurities are typical of electrolyte degradation (LiPF$_6$).

Figure 11:
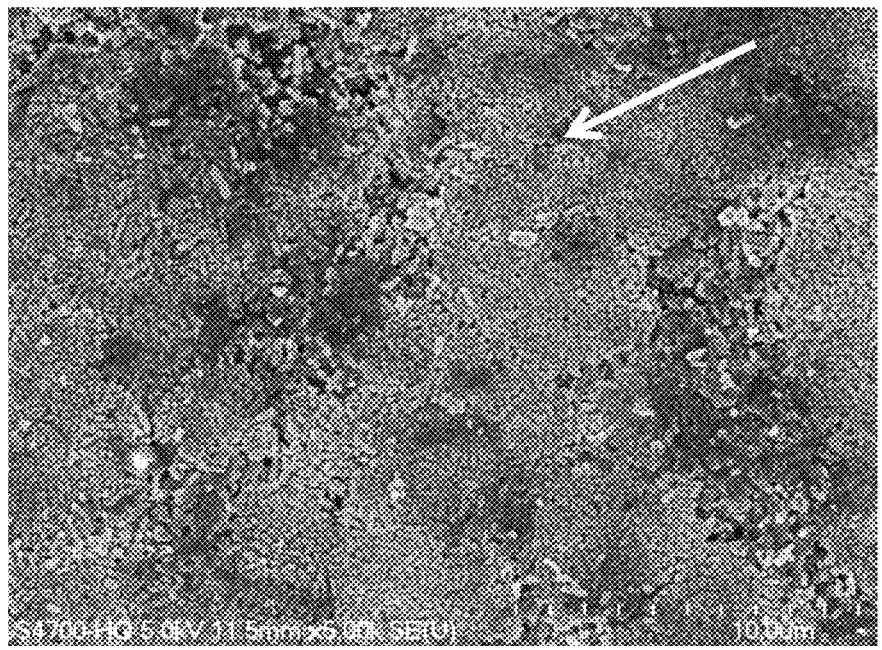
FIG. 11 shows scanning electronic microscopy (SEM) images of the cathode surface (on the electrolyte separator side) after cycling of a LFP/Li cell (a) without indigo and (b) with 1% indigo.
Figure 11:
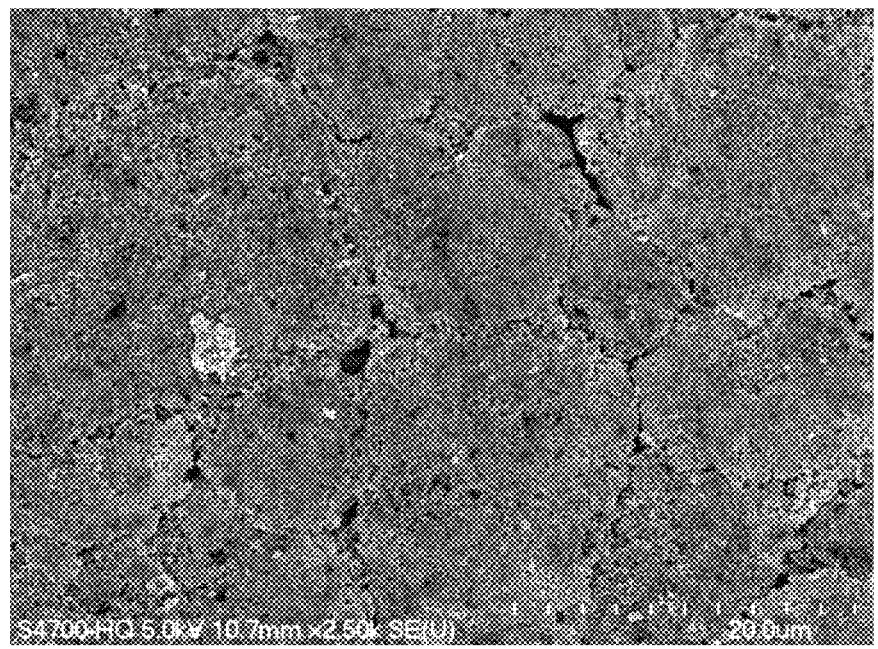

Finally, the cathode surface in contact with the battery separator was analysed by SEM in both Cell B2-a and control Cell A2 after cycling. Images obtained are presented in FIGS. 11 (a) and (b) respectively. When looking at the cell without indigo (FIG. 11(a)), dark zones typically resulting from electrolyte degradation are observed. The image of FIG. 11(b) showing the material using indigo as an additive does not present electrolyte degradation.

Numerous modifications could be made to any of the embodiments described above without departing from the scope of the present invention. Any references, patents or scientific literature documents referred to in this application are incorporated herein by reference in their entirety for all purposes.

The invention claimed is:

1. An electrode material comprising particles of an inorganic electrochemically active material and a compound of any one of Formulae I to IV:

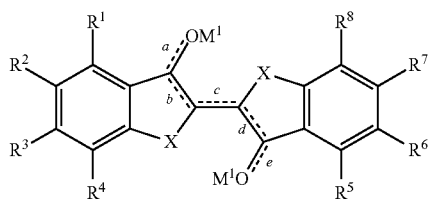

Formula I

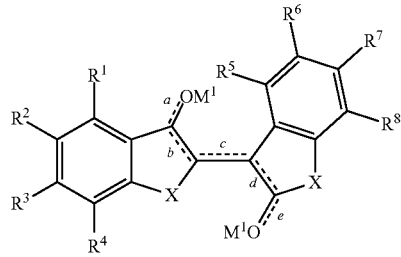

Formula II

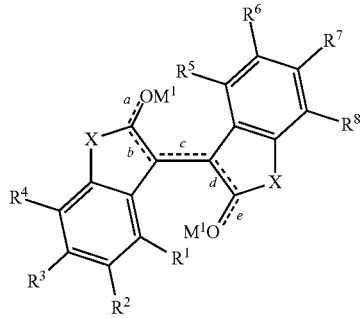

Formula III

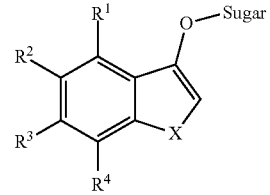

Formula IV wherein,
  $R^1$, $R^2$, $R^3$, $R^4$, $R^5$, $R^6$, $R^7$, and $R^8$ are each independently selected from a hydrogen atom, halogens alkyl groups, haloalkyl groups, cycloalkyl groups, aryl groups, —CN, —NO$_2$, —SO$_2$OM$^2$, —OP(O)(OM$^2$)$_2$, —P(O)(OM$^2$)$_2$, —C(O)OM$^2$, wherein M$^2$ is a cation of an alkali or alkaline earth metal, —OC(O)alkyl groups, —SO$_2$NH$_2$, —SO$_2$NHalkyl groups, and —SO$_2$N(alkyl)$_2$, groups; and
  X is, independently in each occurrence, selected from O, S, NH, NR$^9$, and PH,
    wherein R$^9$ is selected from natural or synthetic carbohydrate and protective groups; and
    "Sugar" denotes a natural or synthetic carbohydrate selected from the group consisting of monosaccharides, disaccharides, oligosaccharides, and polysaccharides; and
  wherein:
    i. a, c and e are single bonds, b and d are double bonds, and M$^1$ is H or a cation of an alkali or alkaline earth metal thereby forming a salt with the oxygen atom it is linked to negatively charged wherein the ratio of cation to the rest of the compound of Formula I provides electroneutrality; or
    ii. a, c and e are double bonds, b and d are single bonds, and M$^1$ is absent;
  or an oxime thereof (i.e. where =OM$^1$ is replaced with =NOH in Formulae I, II or III), a compound of Formula IV where the Sugar is replaced by a hydrogen atom, a geometric isomer thereof, or a carbohydrate which is a monosaccharide, disaccharide, oligosaccharide or a polysaccharide, complex or conjugate thereof.

2. The electrode material of claim 1, wherein X is O, S or NH.

3. The electrode material of claim 1, wherein the compound is of Formula I, II or II, and:
  $R^2$ and $R^6$ are the same and selected from halogens, alkyl groups, haloalkyl groups, —CN, and —SO$_2$OM$^2$;
  $R^3$ and $R^7$ are the same and selected from halogens, alkyl groups, haloalkyl groups, —CN, and —SO$_2$OM$^2$; or
  $R^1$ to $R^8$ are each a hydrogen atom.

4. The electrode material of claim 1, wherein the compound is of Formula IV and:

R² is selected from halogens, alkyl groups, haloalkyl groups, —CN, and —SO₂OM²; or R¹ to R⁴ are each a hydrogen atom.

5. The electrode material of claim 1, wherein the compound is selected from:

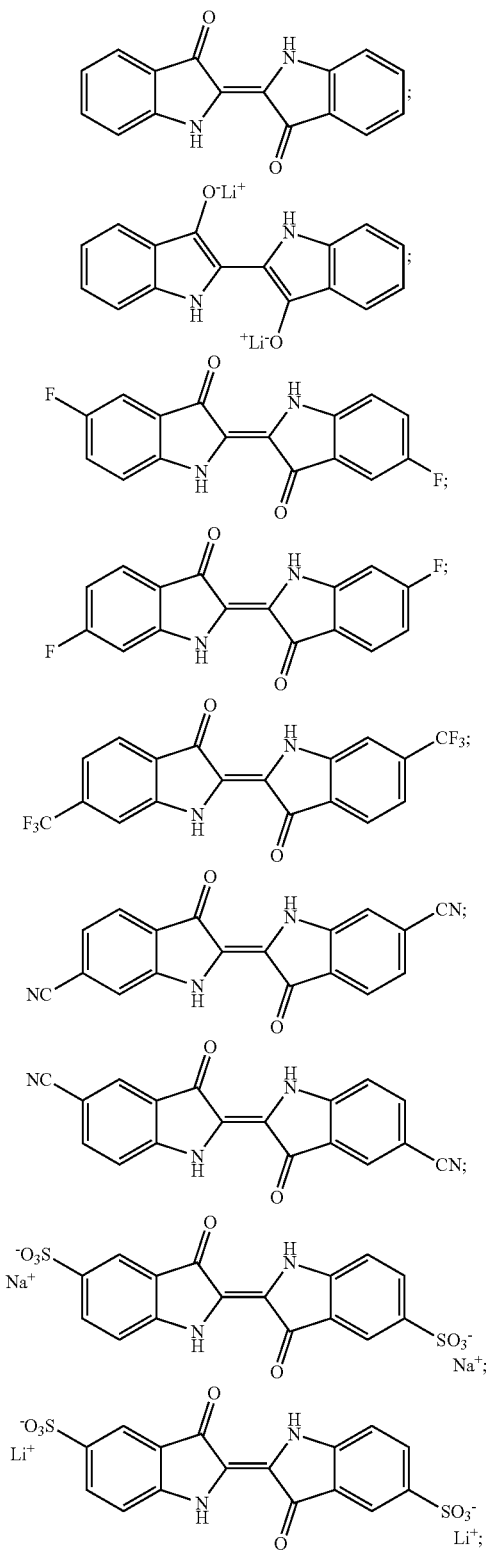

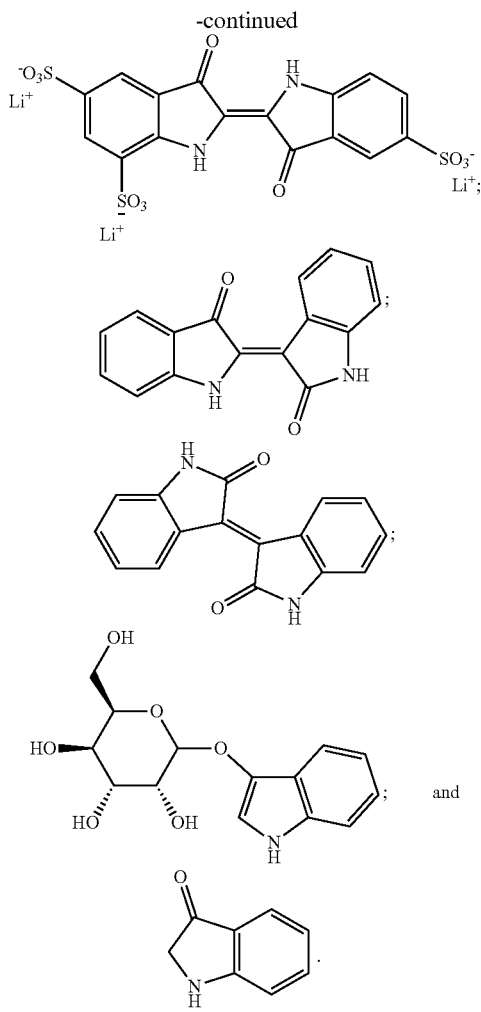

6. The electrode material of claim 1, wherein the compound is selected from indigo blue, indigo carmine, isoindigo, indigopurpurin, indolinedione, and leuco-indigo or a salt thereof.

7. The electrode material of claim 1, wherein the electrochemically active material comprises a material selected from the group consisting of titanates, lithium titanates, lithium metal phosphates, vanadium oxides, and lithium metal oxides.

8. The electrode material of claim 1, wherein the electrochemically active material is
   $TiO_2$, $Li_2TiO_3$, $Li_4Ti_5O_{12}$, $H_2Ti_5O_{11}$ and $H_2Ti_4O_9$, or a combination thereof, or
   $LiM'PO_4$ wherein M' is Fe, Ni, Mn, Co, or a combination thereof, or
   $LiV_3O_8$, $V_2O_5$, $LiMn_2O_4$, $LiM''O_2$, wherein M'' is Mn, Co, Ni, or a combination thereof, or
   $Li(NiM''')O_2$, wherein M''' is Mn, Co, Al, Fe, Cr, Ti, or Zr, or a combination thereof, and
   wherein the electrochemically active material is optionally doped with a compatible element.

9. The electrode material of claim 7, wherein said electrochemically active material is selected from titanates and lithium titanates.

10. The electrode material of claim 8, wherein said electrochemically active material is of the formula $LiM'PO_4$ wherein M' is Fe, Ni, Mn, Co, or a combination thereof, and the electrochemically active material is optionally doped with an element selected from Mg, Al, B, Ti, V, Cr, Cu, Zn, Mo, Sn, Ca, Sr, W, and combinations thereof.

11. The electrode material of claim 10, wherein said electrochemically active material is $LiMn_xFe_{1-x}PO_4$, wherein $0<x<1$, the electrochemically active material being optionally doped with a Co, Ni, Mg, Al, B, Ti, V, Cr, Cu, Zn, Mo, Sn, Ca, Sr, W, or a combination thereof.

12. The electrode material of claim 8, wherein said electrochemically active material is $LiM''O_2$, wherein M'' is Mn, Co, Ni, or a combination thereof.

13. The electrode material of claim 1, wherein said particles are further coated with a conductive agent.

14. The electrode material of claim 1, further comprising a conductive agent and/or a binder.

15. The electrode material of claim 1, wherein said compound is in a concentration from 0.1 wt % to 5 wt %.

16. A process for producing an electrode comprising an electrode material as defined in claim 1, comprising the steps of:
    a) mixing, in any order, the compound, the particles of electrochemically active material, and a binder in a solvent to obtain a slurry;
    b) casting the slurry obtained in step (a) on a substrate; and
    c) drying the casted slurry.

17. An electrode comprising the electrode material as defined in claim 1, on a current collector.

18. The electrode of claim 17, wherein the current collector is aluminum or an alloy having aluminum as the main component or a conductive polymer.

19. An electrochemical cell comprising an electrode as defined in claim 17, an electrolyte and a counter-electrode.

20. An electrochemical generator or an electrochemical accumulator comprising an electrochemical cell as defined in claim 19.

21. The electrode material of claim 1, wherein X is NH.

22. The electrode material of claim 10, wherein said electrochemically active material is $LiFePO_4$.

23. The electrode material of claim 8, wherein said electrochemically active material is of a formula $LiNi_wMn_yCo_zO_2$, wherein $w+y+z=1$.

24. The electrode material of claim 1, further comprising a conductive agent and/or a binder, the binder comprising a cellulose-derived binder, a water-soluble binder, or a fluorine-containing polymeric binder.

25. The electrode material of claim 1, wherein said compound is in a concentration from 0.1 wt % to 2 wt %, in the electrode material.

* * * * *